US012594422B2

(12) United States Patent
Xu et al.

(10) Patent No.: US 12,594,422 B2
(45) Date of Patent: Apr. 7, 2026

(54) SYSTEMS AND DEVICES FOR TREATING EQUILIBRIUM DISORDERS AND IMPROVING GAIT AND BALANCE

(71) Applicant: Starkey Laboratories, Inc., Eden Prairie, MN (US)

(72) Inventors: Buye Xu, Sammamish, WA (US); Justin R. Burwinkel, Eden Prairie, MN (US); Jason A. Galster, Studio City, CA (US); Peggi S. Cross, Tucson, AZ (US); Jay Stewart, Eden Prairie, MN (US); Martin McKinney, Minneapolis, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 576 days.

(21) Appl. No.: 17/626,645

(22) PCT Filed: Jul. 10, 2020

(86) PCT No.: PCT/US2020/041573
§ 371 (c)(1),
(2) Date: Jan. 12, 2022

(87) PCT Pub. No.: WO2021/011364
PCT Pub. Date: Jan. 21, 2021

(65) Prior Publication Data
US 2022/0233855 A1 Jul. 28, 2022

(51) Int. Cl.
*A61N 1/36* (2006.01)

(52) U.S. Cl.
CPC ..... *A61N 1/36003* (2013.01); *A61N 1/36036* (2017.08)

(58) Field of Classification Search
CPC ........................ A61N 1/36003; A61N 1/36036
See application file for complete search history.

(56) References Cited

U.S. PATENT DOCUMENTS

| | | | |
|---|---|---|---|
| 4,984,579 A | 1/1991 | Burgert et al. | |
| 5,024,612 A | 6/1991 | Van et al. | |

(Continued)

FOREIGN PATENT DOCUMENTS

| | | |
|---|---|---|
| RU | 2392013 | 6/2010 |
| WO | 2010138915 | 12/2010 |

(Continued)

OTHER PUBLICATIONS

"Gait Disorders and Abnormalities" https://my.clevelandclinic.org/health/diseases/21092-gait-disorders (Year: 2025).*

(Continued)

*Primary Examiner* — Unsu Jung
*Assistant Examiner* — Laura Hodge
(74) *Attorney, Agent, or Firm* — Pauly, DeVries Smith & Deffner LLC

(57) ABSTRACT

Embodiments herein relate to systems, devices and methods for the treatment of equilibrium disorders and improving gait and balance. In an embodiment, a method of treating an equilibrium disorder is included. The method can include monitoring device wearer movement with a movement sensor, identifying a movement pattern consistent with an equilibrium disorder, estimating characteristics of the equilibrium disorder, and applying stimulation to at least one of the right ear, left ear, or brainstem of the device wearer of an ear-worn device. Other embodiments are also included herein.

20 Claims, 13 Drawing Sheets

(56) References Cited

U.S. PATENT DOCUMENTS

| | | | |
|---|---|---|---|
| 6,314,324 B1 | 11/2001 | Lattner et al. | |
| 6,358,272 B1 | 3/2002 | Wilden | |
| 8,262,717 B2 | 9/2012 | Rogers et al. | |
| 8,355,788 B2 | 1/2013 | Mechlenburg et al. | |
| 9,149,222 B1 * | 10/2015 | Zets | A61B 5/4023 |
| 9,167,356 B2 | 10/2015 | Higgins et al. | |
| 9,339,649 B2 | 5/2016 | Cushing et al. | |
| 9,848,273 B1 | 12/2017 | Helwani et al. | |
| 9,849,026 B2 | 12/2017 | Rogers et al. | |
| 10,888,696 B2 | 1/2021 | Risi et al. | |
| 2004/0006287 A1 * | 1/2004 | Epley | A61B 5/11 |
| | | | 600/595 |
| 2007/0112287 A1 | 5/2007 | Fancourt et al. | |
| 2008/0208266 A1 | 8/2008 | Lesser et al. | |
| 2010/0198282 A1 * | 8/2010 | Rogers | A61F 7/007 |
| | | | 607/3 |
| 2012/0101411 A1 * | 4/2012 | Hausdorff | A61B 5/1117 |
| | | | 600/595 |
| 2012/0316624 A1 | 12/2012 | Smith et al. | |
| 2015/0039057 A1 | 2/2015 | Della et al. | |
| 2017/0165481 A1 * | 6/2017 | Menon | A61N 1/36139 |
| 2018/0228404 A1 | 8/2018 | Bhunia et al. | |
| 2018/0317837 A1 | 11/2018 | Burwinkel et al. | |

FOREIGN PATENT DOCUMENTS

| | | | |
|---|---|---|---|
| WO | WO-2011161562 A1 * | 12/2011 | A61N 1/0456 |
| WO | 2012083098 | 6/2012 | |
| WO | WO-2012083098 A1 * | 6/2012 | A61F 7/007 |
| WO | WO-2013172935 A2 * | 11/2013 | A61N 1/0456 |
| WO | WO-2018013398 A1 * | 1/2018 | A61B 5/1116 |
| WO | WO-2018106839 A2 * | 6/2018 | A61F 11/00 |
| WO | WO-2019005774 A1 * | 1/2019 | A61K 45/06 |
| WO | 2021011364 | 1/2021 | |

OTHER PUBLICATIONS

"International Preliminary Report on Patentability," for PCT Application No. PCT/US2020/041573 mailed Jan. 27, 2022 (8 pages).

"International Search Report and Written Opinion," for PCT Application No. PCT/US2020/041573 mailed Oct. 16, 2020 (14 pages).

"MASPARK," Automatic gait control system by Fraunhofer Portugal 2015-2017 (2 pages).

Bachlin, M., et al. "Online Detection of Freezing of Gait in Parkinson's Disease Patients: A Performance Characterization.," Proc 4th Int ICST Conf body Area Netowrks. lcst; 2009 (8 pages).

Cushing, Sharon L., et al. "A Test of Static and Dynamic Balance Function in Children with Cochlear Implants," Arch Otolaryngol Head Neck Surg. 2008;134(1): 34-38 (5 pages).

Della Santina, Charles C., et al. "A Multichannel Semicircular Canal Neural Prosthesis Using Electrical Stimulation to Restore 3-D Vestibular Sensation," IEEE Transactions on Biomedical Engineering, vol. 54, No. 6, Jun. 2007 (15 pages).

Lawson, J., et al. "Positional vertigo in a falls service," Age and Ageing (2008) 37(5), 585-588 (5 pages).

Rodriguez-Martin, D., et al. "Home detection of freezing of gait using support vector machines through a single waist-worn triaxial accelerometer," PLoS One 2017; 12(2):e0171764 (8 pages).

Ross, J. M., et al. "Auditory white noise reduces age-related fluctuations in balance," Abstract Only Neuroscience Letters 2016 (630), 216-221 retrieved from https://doi.org/10.1016/j.neulet.2016.07.060 (2 pages).

* cited by examiner

SYSTEMS AND DEVICES FOR TREATING EQUILIBRIUM DISORDERS AND IMPROVING GAIT AND BALANCE

This application is being filed as a PCT International Patent application on Jul. 10, 2020 in the name of Starkey Laboratories, Inc., a U.S. national corporation, applicant for the designation of all countries, and Buye Xu, a Citizen of China, and Justin R. Burwinkel, a U.S. Citizen, and Jason A. Galster, a U.S. Citizen, and Peggi S. Cross, a U.S. Citizen, and Jay Stewart, a U.S. Citizen, and Martin McKinney, a U.S. Citizen, inventor(s) for the designation of all countries, and claims priority to U.S. Provisional Patent Application No. 62/873,598 filed Jul. 12, 2019, the contents of which are herein incorporated by reference in its entirety.

FIELD

Embodiments herein relate to the treatment of equilibrium disorders and improving gait and balance. More specifically, embodiments herein relate to systems, devices and methods for the treatment of equilibrium disorders and improving gait and balance.

BACKGROUND

The human vestibular system provides a sense of balance and information about body position that allows for the reflexive initiation of compensatory movements in response to both self-induced and external forces. The inner ear forms part of the vestibular system and functions as a biological accelerometer and inertial guidance device, reporting information about the motions and position of the head and body to integrative centers located in the brainstem, cerebellum, and somatic sensory cortices. The information generated by the vestibular system makes it a key component in both postural reflexes and eye movements.

Equilibrium disorders can result in adverse effects on balance, gait, control of eye movements when the head is moving, and sense of orientation in space. As such, treatment of equilibrium disorders holds the promise of improvements in balance, gait, control of eye movements, and sense of orientation in space, amongst other things.

SUMMARY

Embodiments herein relate to systems, devices and methods for the treatment of equilibrium disorders and improving gait and balance. In a first aspect, a method of treating an equilibrium disorder is included, the method including monitoring device wearer movement with a movement sensor; identifying a movement pattern consistent with an equilibrium disorder; estimating characteristics of the equilibrium disorder; and applying stimulation to at least one of the right ear, left ear, or brainstem of the device wearer of an ear-worn device.

In a second aspect, in addition to one or more of the preceding or following aspects, or in the alternative to some aspects, the characteristics of the equilibrium disorder can relate to at least one of a site of a lesion, the device wearer's perceived head position versus actual head position, and the device wearer's perceived head movement versus actual head movement.

In a third aspect, in addition to one or more of the preceding or following aspects, or in the alternative to some aspects, the stimulation can include an excitatory vestibular stimulus.

In a fourth aspect, in addition to one or more of the preceding or following aspects, or in the alternative to some aspects, the stimulation can include at least one of caloric stimulation, nerve stimulation, auditory stimulation and electromagnetic stimulation.

In a fifth aspect, in addition to one or more of the preceding or following aspects, or in the alternative to some aspects, the stimulation can include an inhibitory vestibular stimulus.

In a sixth aspect, in addition to one or more of the preceding or following aspects, or in the alternative to some aspects, the method can further include monitoring device wearer movement with the movement sensor after the application of stimulation, and adjusting ongoing application of the stimulation based on detected movement.

In a seventh aspect, in addition to one or more of the preceding or following aspects, or in the alternative to some aspects, the device wearer movement can include eye movement.

In an eighth aspect, in addition to one or more of the preceding or following aspects, or in the alternative to some aspects, the movement pattern can include nystagmus.

In a ninth aspect, in addition to one or more of the preceding or following aspects, or in the alternative to some aspects, the device wearer movement can include postural sway.

In a tenth aspect, in addition to one or more of the preceding or following aspects, or in the alternative to some aspects, the device wearer movement can include head movement.

In an eleventh aspect, in addition to one or more of the preceding or following aspects, or in the alternative to some aspects, the movement sensor can include an electrooculography (EOG) sensor, a videooculography (VOG) sensor, or a videonystagmography sensor.

In a twelfth aspect, in addition to one or more of the preceding or following aspects, or in the alternative to some aspects, the movement sensor can include an IMU.

In a thirteenth aspect, in addition to one or more of the preceding or following aspects, or in the alternative to some aspects, the movement sensor can be part of an ear-worn device.

In a fourteenth aspect, in addition to one or more of the preceding or following aspects, or in the alternative to some aspects, identifying a movement pattern consistent with an equilibrium disorder can be performed with an ear-worn device.

In a fifteenth aspect, in addition to one or more of the preceding or following aspects, or in the alternative to some aspects, estimating the characteristics of the equilibrium disorder can be performed with an ear-worn device.

In a sixteenth aspect, in addition to one or more of the preceding or following aspects, or in the alternative to some aspects, estimating the characteristics of the equilibrium disorder includes determining aspects of nystagmus which include two or more of fast phase velocity, slow phase velocity, direction of nystagmus beating, rotary nystagmus, directional preponderance, and gaze angle.

In a seventeenth aspect, a system including an ear-worn device is included having a control circuit; sensor package in communication with the control circuit; a power supply circuit in electrical communication with the control circuit. The system can be configured to monitor device wearer movement with a movement sensor, identify a movement pattern consistent with an equilibrium disorder, estimate the characteristics of the equilibrium disorder, and apply stimulation to at least one of the right ear, left ear, and brainstem using the ear-worn device.

In an eighteenth aspect, in addition to one or more of the preceding or following aspects, or in the alternative to some aspects, the stimulation can include an excitatory vestibular stimulus.

In a nineteenth aspect, in addition to one or more of the preceding or following aspects, or in the alternative to some aspects, the stimulation can include at least one of caloric stimulation, nerve stimulation, auditory stimulation and electromagnetic stimulation.

In a twentieth aspect, in addition to one or more of the preceding or following aspects, or in the alternative to some aspects, the stimulation can include an inhibitory vestibular stimulus.

In a twenty-first aspect, in addition to one or more of the preceding or following aspects, or in the alternative to some aspects, the system can further be configured to monitor device wearer movement with the movement sensor after the application of stimulation and adjusting ongoing application of stimulation based on detected movement.

In a twenty-second aspect, in addition to one or more of the preceding or following aspects, or in the alternative to some aspects, the device wearer movement can include eye movement.

In a twenty-third aspect, in addition to one or more of the preceding or following aspects, or in the alternative to some aspects, the movement pattern can include nystagmus.

In a twenty-fourth aspect, in addition to one or more of the preceding or following aspects, or in the alternative to some aspects, the device wearer movement can include postural sway.

In a twenty-fifth aspect, in addition to one or more of the preceding or following aspects, or in the alternative to some aspects, the device wearer movement can include head movement.

In a twenty-sixth aspect, in addition to one or more of the preceding or following aspects, or in the alternative to some aspects, the movement sensor can include an electrooculography (EOG) sensor or a or a videonystagmography sensor.

In a twenty-seventh aspect, in addition to one or more of the preceding or following aspects, or in the alternative to some aspects, the movement sensor can include an IMU.

In a twenty-eighth aspect, in addition to one or more of the preceding or following aspects, or in the alternative to some aspects, estimating the characteristics of the equilibrium disorder includes estimating the lateral distribution of the equilibrium disorder.

In a twenty-ninth aspect, in addition to one or more of the preceding or following aspects, or in the alternative to some aspects, estimating the characteristics of an equilibrium disorder includes determining aspects of nystagmus including two or more of fast phase velocity, slow phase velocity, direction of nystagmus beating, directional preponderance, and gaze angle.

In a thirtieth aspect, in addition to one or more of the preceding or following aspects, or in the alternative to some aspects, the ear-worn device further can include a microphone and an electroacoustic transducer.

In a thirty-first aspect, in addition to one or more of the preceding or following aspects, or in the alternative to some aspects, the ear-worn device can further include a heating element or a heat sink.

In a thirty-second aspect, a method of improving gait and/or balance of a device wearer is included, the method including monitoring device wearer movement with a movement sensor, identifying a movement pattern consistent with sustained cyclical strides, evaluating the gait and/or balance of the device wearer by analyzing data from the movement sensor, applying auditory stimulation and/or auditory feedback to at least one of the right or left ear using an ear-worn device.

In a thirty-third aspect, in addition to one or more of the preceding or following aspects, or in the alternative to some aspects, the auditory stimulation can include sound with substantially equal volume across a broad frequency spectrum.

In a thirty-fourth aspect, in addition to one or more of the preceding or following aspects, or in the alternative to some aspects, the auditory stimulation can include white noise at an intensity of at least 60 dB SPL.

In a thirty-fifth aspect, in addition to one or more of the preceding or following aspects, or in the alternative to some aspects, the auditory stimulation can include pink noise at an intensity of at least 60 dB SPL.

In a thirty-sixth aspect, in addition to one or more of the preceding or following aspects, or in the alternative to some aspects, the method further including ceasing the auditory stimulation when the movement pattern consistent with sustained cyclical strides ceases.

In a thirty-seventh aspect, in addition to one or more of the preceding or following aspects, or in the alternative to some aspects, monitoring device wearer movement with a movement sensor can be performed by an ear worn device.

In a thirty-eighth aspect, in addition to one or more of the preceding or following aspects, or in the alternative to some aspects, wherein identifying a movement pattern consistent with sustained cyclical strides is performed by an ear worn device.

In a thirty-ninth aspect, in addition to one or more of the preceding or following aspects, or in the alternative to some aspects, wherein evaluating the gait and/or balance of the device wearer by analyzing data from the movement sensor is performed by an ear worn device.

In a fortieth aspect, a method of improving gait and/or balance of an ear-worn device wearer is included, the method monitoring device wearer movement with an ear-worn device, the ear-worn device can include a control circuit, an electroacoustic transducer for generating sound in electrical communication with the control circuit, a power supply circuit in electrical communication with the control circuit, and at least one of a microphone in electrical communication with the control circuit; and a movement sensor in electrical communication with the control circuit. The method can further include identifying a movement pattern consistent with sustained cyclical strides, and applying cyclical auditory stimulation or feedback to at least one of the right or left ear at a cyclical frequency using the ear-worn device, wherein the cyclical frequency equals an ambulatory pace.

In a forty-first aspect, in addition to one or more of the preceding or following aspects, or in the alternative to some aspects, the cyclical frequency can be from 0.5 Hz to 3 Hz.

In a forty-second aspect, in addition to one or more of the preceding or following aspects, or in the alternative to some aspects, the method can further include identifying a movement pattern consistent with sustained cyclical strides includes identifying a movement pattern consistent with sustained cyclical strides that is sustained for at least 3 seconds.

In a forty-third aspect, in addition to one or more of the preceding or following aspects, or in the alternative to some aspects, the method can further include analyzing data from the movement sensor to determine a sustained cyclical stride pace of the device wearer.

In a forty-fourth aspect, in addition to one or more of the preceding or following aspects, or in the alternative to some aspects, the method can further include applying cyclical auditory stimulation to at least one of the right or left ear using the ear-worn device at a pace that is faster than the determined sustained cyclical stride pace when the determined sustained cyclical stride pace is below a threshold value.

In a forty-fifth aspect, in addition to one or more of the preceding or following aspects, or in the alternative to some aspects, the method can further include adaptively determining a threshold value for the device wearer.

In a forty-sixth aspect, in addition to one or more of the preceding or following aspects, or in the alternative to some aspects, the method can further include applying cyclical auditory stimulation to at least one of the right or left ear using the ear-worn device at a pace that is slower than the determined sustained cyclical stride pace when the determined sustained cyclical stride pace is above a threshold value.

In a forty-seventh aspect, in addition to one or more of the preceding or following aspects, or in the alternative to some aspects, the method can further include storing the determined sustained cyclical stride pace along with a timestamp.

In a forty-eighth aspect, in addition to one or more of the preceding or following aspects, or in the alternative to some aspects, the method can further include calculating a trend in the determined sustained cyclical stride pace over time.

In a forty-ninth aspect, in addition to one or more of the preceding or following aspects, or in the alternative to some aspects, the method can further include sending an alert to a third party when the trend indicates a possible decompensation event.

In a fiftieth aspect, in addition to one or more of the preceding or following aspects, or in the alternative to some aspects, the method can further include providing spoken word feedback to the device wearer.

In a fifty-first aspect, in addition to one or more of the preceding or following aspects, or in the alternative to some aspects, the method can further include providing spoken word feedback to the device wearer regarding the identified movement pattern.

In a fifty-second aspect, in addition to one or more of the preceding or following aspects, or in the alternative to some aspects, the method can further include providing spoken word feedback to the device wearer regarding recommended changes to the identified movement pattern.

In a fifty-third aspect, in addition to one or more of the preceding or following aspects, or in the alternative to some aspects, the method can further include monitoring for movement changes during the spoken word feedback indicative of a stops walking when talking response.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
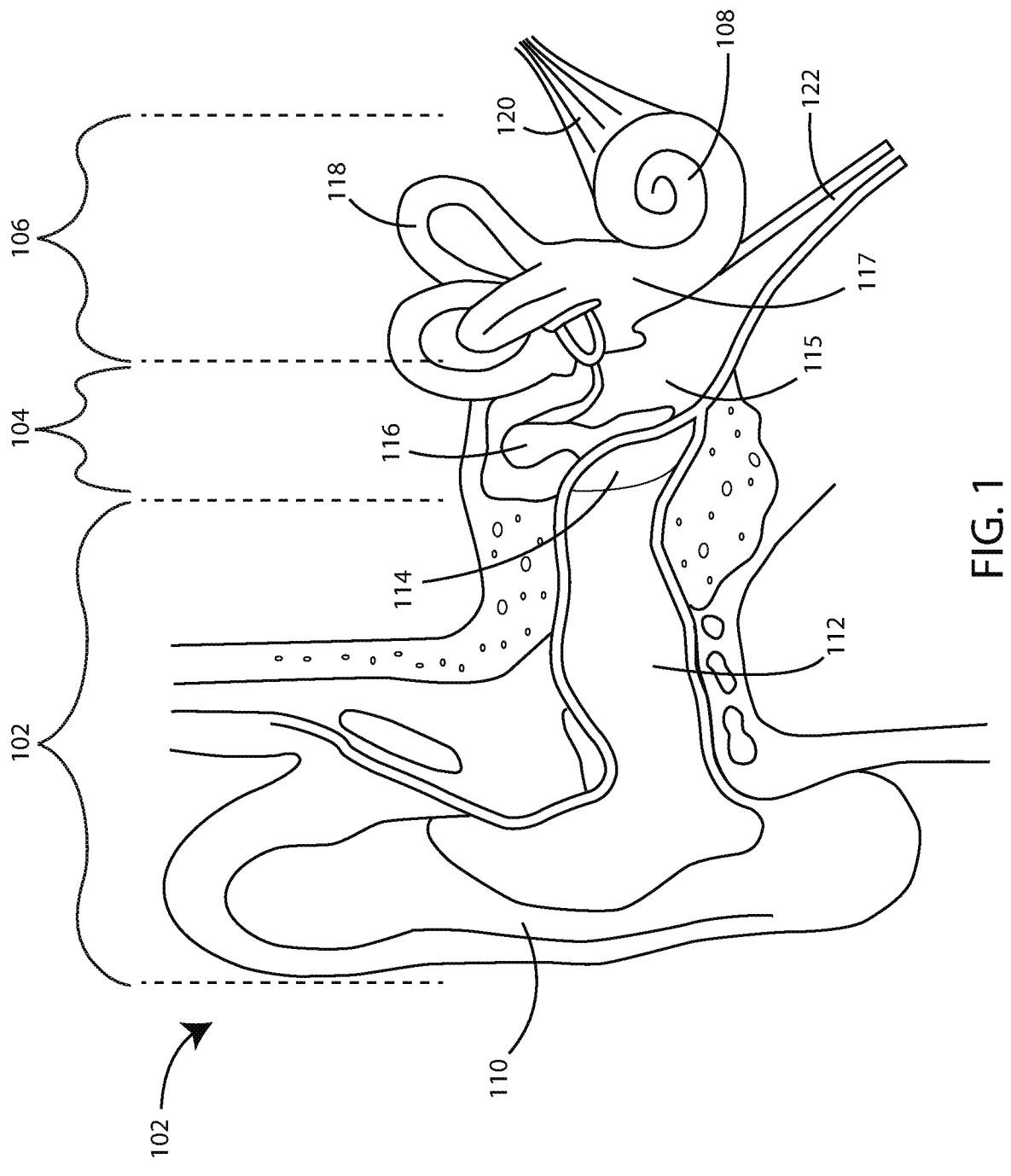
FIG. 1 is a partial cross-sectional view of ear anatomy.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, equilibrium disorders can result in adverse effects on balance, gait, control of eye movements when the head is moving, and sense of orientation in space. Various embodiments herein can be used to treat, attenuate, and/or ameliorate an equilibrium disorder. Various embodiments herein can be used to treat, attenuate, and/or ameliorate a vestibular pathology. Various embodiments herein can also be used to treat, attenuate, or otherwise ameliorate the effects of the equilibrium disorder including, but not limited to, improving balance, gait, and the like.

As a more specific example, in accordance with various embodiments herein, a method of treating equilibrium disorders is included. In some scenarios, the method can include monitoring device wearer movement with a movement sensor and then identifying a movement pattern consistent with an equilibrium disorder. In some scenarios, the method can then include estimating characteristics of the equilibrium disorder. The characteristics of the equilibrium disorder can relate to at least one of a predicted site of a lesion, the device wearer's perceived head position versus actual head position, the device wearer's perceived head movement versus actual movement, the device wearer's eye movements, and the degree of the wearer's vestibular asymmetry, and applying stimulation to at least one of the right ear, left ear, or brainstem of the device wearer of an ear-worn device.

In various embodiments herein, an ear-worn medical device is included. The ear-worn device can include a control circuit, a sensor package in communication with the control circuit, and a power supply circuit in electrical communication with the control circuit. The ear-worn device can be configured to monitor device wearer movement with a movement sensor, identify a movement pattern consistent with an equilibrium disorder, estimate the characteristics of the equilibrium disorder, and apply stimulation to at least one of the right ear, left ear, and brainstem using an ear-worn device.

In various embodiments herein, a method of improving gait and/or balance of a device wearer is included. The method can include monitoring device wearer movement with a movement sensor, identifying a movement pattern consistent with sustained cyclical strides, evaluating the gait and/or balance of the device wearer by analyzing data from the movement sensor, and applying auditory stimulation and/or auditory feedback to at least one of the right or left ear using an ear-worn device.

In various embodiments herein, a method of improving gait and/or balance of an ear-worn device wearer. The method can include monitoring device wearer movement with an ear-worn device, identifying a movement pattern consistent with sustained cyclical strides, and applying cyclical auditory stimulation or feedback to at least one of the right or left ear at a cyclical frequency using the ear-worn device, wherein the cyclical frequency equals an ambulatory pace.

Equilibrium disorders treatable herein can include, but are not limited to, vestibular pathologies. Equilibrium disorders treatable herein and/or causing symptoms that can be treated herein can include, but are not limited to, acoustic neuroma, idiopathic dizziness and imbalance, autoimmune mediated inner ear disease, benign paroxysmal positional vertigo (BPPV), bilateral vestibular hypofunction, cerebellar ataxia, neuropathy, vestibular areflexia (CANVAS), cervicogenic dizziness, cholesteatoma, enlarged vestibular aqueduct syndrome (EVAS), vestibulopathy, labyrinthitis, vestibular neuritis, migraine-associated vertigo (MAV), Meniere's disease, neurotoxic vestibulopathy, otosclerosis, perilymph fistula, persistent postural perceptual dizziness (PPPD), secondary endolymphatic hydrops (SHE), superior semicircular canal dehiscence, tinnitus secondary to a vestibular pathology, vestibular hyperacusis, vertebrobasilar insufficiency, and the like.

The term "ear-worn device" as used herein shall refer to devices that can aid a person with impaired hearing. The term "ear-worn device" shall also refer to devices that can produce optimized or processed sound for persons with normal hearing. Ear-worn devices herein can include hearing assistance devices. Ear-worn devices herein can include, but are not limited to, behind-the-ear (BTE), in-the ear (ITE), in-the-canal (ITC), invisible-in-canal (IIC), receiver-in-canal (RIC), receiver in-the-ear (RITE) and completely-in-the-canal (CIC) type hearing assistance devices. In some embodiments, the ear-worn device can be a hearing aid falling under 21 C.F.R. § 801.420. In another example, the ear-worn device can include one or more Personal Sound Amplification Products (PSAPs). In another example, the ear-worn device can include one or more cochlear implants, cochlear implant magnets, cochlear implant transducers, and cochlear implant processors. In another example, the hearing assistance device can include one or more "hearable" devices that provide various types of functionality. In other examples, ear-worn devices can include other types of devices that are wearable in, on, or in the vicinity of the user's ears. In other examples, ear-worn devices can include other types of devices that are implanted or otherwise osseointegrated with the user's skull; wherein the device is able to facilitate stimulation of the wearer's ears via the bone conduction pathway. In another example, the hearing assistance device can include an auditory brainstem implant, a cranial nerve (e.g., CN VIII) implant, and the like.

Referring now to FIG. 1, a partial cross-sectional view of ear anatomy 100 is shown. The three parts of the ear anatomy 100 are the outer ear 102, the middle ear 104 and the inner ear 106. The inner ear 106 includes the cochlea 108, vestibule 117, and semicircular canals 118, and auditory nerve 120. ('Cochlea' means 'snail' in Latin; the cochlea gets its name from its distinctive coiled up shape.) The outer ear 102 includes the pinna 110, ear canal 112, and the tympanic membrane 114 (or eardrum). The middle ear 104 includes the tympanic cavity 115, and auditory bones 116 (malleus, incus, stapes). The pharyngotympanic tube 122 is in fluid communication with the eustachian tube and helps to control pressure within the middle ear generally making it equal with ambient air pressure.

Sound waves enter the ear canal 112 and cause the tympanic membrane 114 vibrate. This action moves the tiny chain of auditory bones 116 (ossicles—malleus, incus, stapes) in the middle ear 104. The last bone in this chain contacts the membrane window of the cochlea 108 and makes the fluid in the cochlea 108 move. The fluid movement then triggers a response in the auditory nerve 120.

Ear-worn devices, including hearing aids and hearables (e.g., wearable earphones), can include an enclosure, such as a housing or shell, within which internal components are disposed. Components of an ear-worn device herein can include a control circuit, digital signal processor (DSP), memory (such as non-volatile memory), power management circuitry, a data communications bus, one or more communication devices (e.g., a radio, a near-field magnetic induction device), one or more antennas, one or more microphones, a receiver/speaker, and various sensors as described in greater detail below. More advanced ear-worn devices can incorporate a long-range communication device, such as a BLUETOOTH® transceiver or other type of radio frequency (RF) transceiver.

Figure 2:
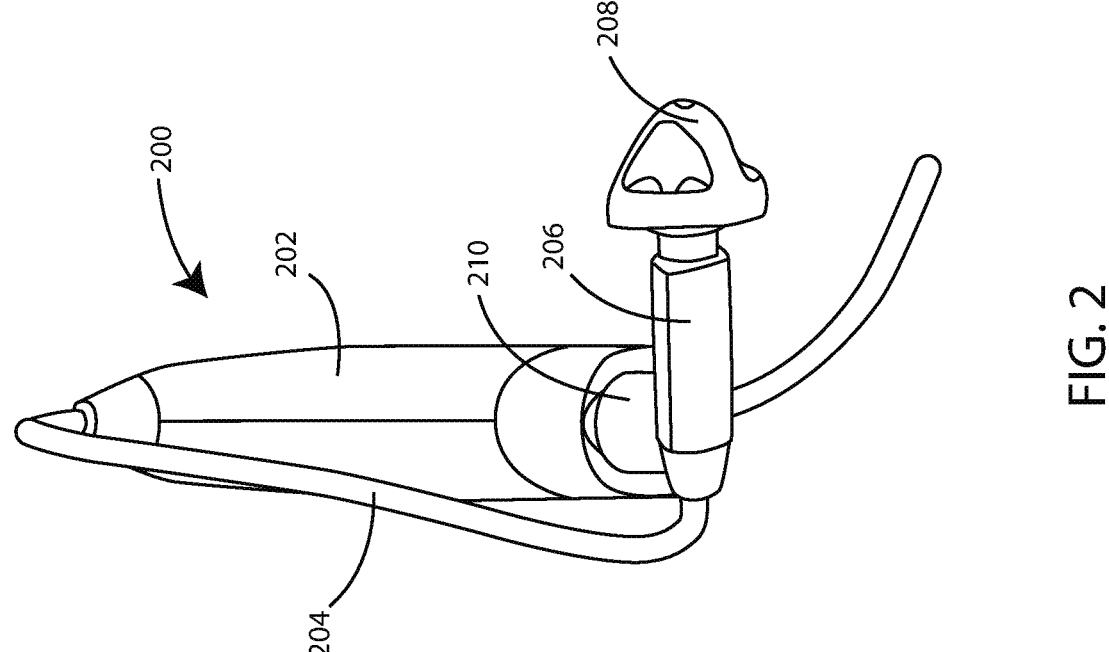
FIG. 2 is a schematic view of an ear-worn device in accordance with various embodiments herein.

Referring now to FIG. 2, a schematic view of an ear-worn device 200 is shown in accordance with various embodiments herein. The ear-worn device 200 can include a hearing device housing 202. The hearing device housing 202 can define a battery compartment 210 into which a battery can be disposed to provide power to the device. The ear-worn device 200 can also include a receiver 206 adjacent to an earbud 208. The receiver 206 an include a component that converts electrical impulses into sound, such as an electroacoustic transducer, speaker, or loud speaker. A cable 204 or connecting wire can include one or more electrical conductors and provide electrical communication between components inside of the hearing device housing 202 and components inside of the receiver 206.

The ear-worn device 200 shown in FIG. 2 is a receiver-in-canal type device and thus the receiver is designed to be placed within the ear canal. However, it will be appreciated that may different form factors for ear-worn devices are contemplated herein. As such, ear-worn devices herein can include, but are not limited to, behind-the-ear (BTE), in-the ear (ITE), in-the-canal (ITC), invisible-in-canal (IIC), receiver-in-canal (RIC), receiver in-the-ear (RITE) and completely-in-the-canal (CIC) type ear-worn devices.

Ear-worn devices of the present disclosure can incorporate an antenna arrangement coupled to a high-frequency radio, such as a 2.4 GHz radio. The radio can conform to an IEEE 802.11 (e.g., WIFI®) or BLUETOOTH® (e.g., BLE, BLUETOOTH® 4.2 or 5.0) specification, for example. It is understood that ear-worn devices of the present disclosure can employ other radios, such as a 900 MHz radio or radios operating at other frequencies or frequency bands. Ear-worn devices of the present disclosure can be configured to receive streaming audio (e.g., digital audio data or files) from an electronic or digital source and/or play audio from memory. Representative electronic/digital sources (also referred to herein as accessory devices) include an assistive listening system, a TV streamer, a remote microphone, a remote control, a radio, a smartphone, a cell phone/entertainment device (CPED) or other electronic device that serves as a source of digital audio data or files. Systems herein can also include these types of accessory devices as well as other types of devices.

Figure 3:
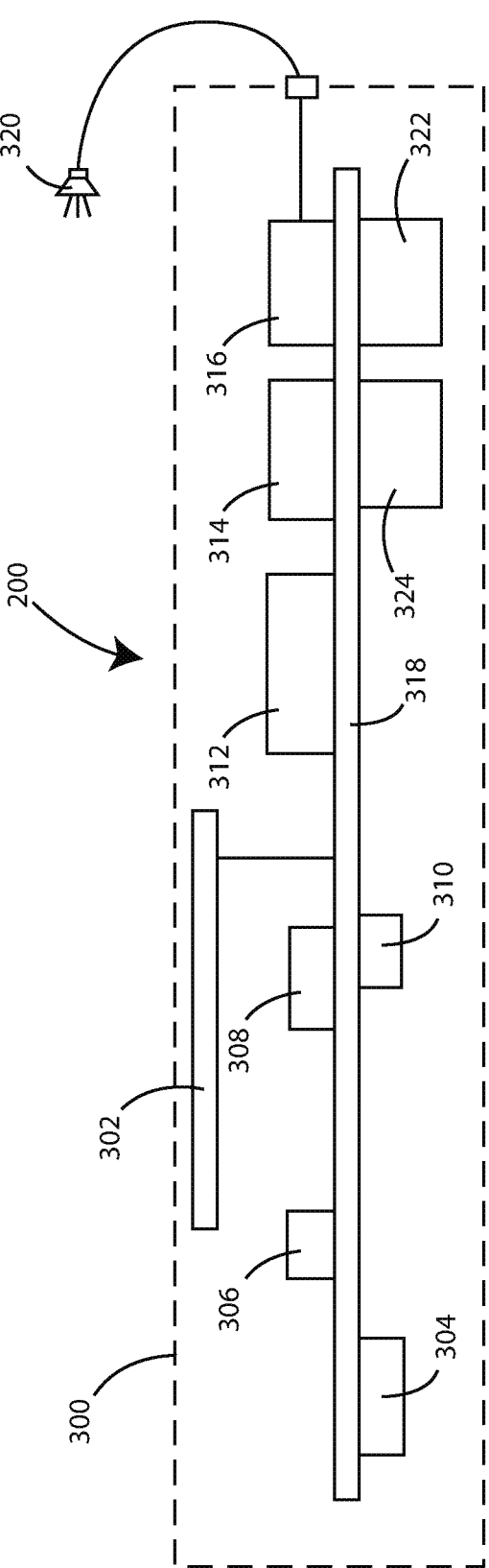
FIG. 3 is a schematic view of various components of an ear-worn device in accordance with various embodiments herein.

Referring now to FIG. 3, a schematic block diagram is shown with various components of an ear-worn device in accordance with various embodiments. It will be appreciated that many of these components can be integrated in an integrated circuit, such as with a system-on-a-chip (SOC) integration, or can exist as separate components. The block diagram of FIG. 3 represents a generic ear-worn device for purposes of illustration. The ear-worn device 200 shown in FIG. 3 includes several components electrically connected to a flexible mother circuit 318 (e.g., flexible mother board) which is disposed within housing 300. A power supply circuit 304 can include a battery and can be electrically connected to the flexible mother circuit 318 and provides power to the various components of the ear-worn device 200. One or more microphones 306 are electrically connected to the flexible mother circuit 318, which provides electrical communication between the microphones 306 and a digital signal processor (DSP) 312. Among other components, the DSP 312 incorporates or is coupled to audio signal processing circuitry configured to implement various functions described herein. A sensor package 314 can be coupled to the DSP 312 via the flexible mother circuit 318. The sensor package 314 can include one or more different specific types of sensors such as those described in greater detail below. One or more user switches 310 (e.g., on/off, volume, mic directional settings) are electrically coupled to the DSP 312 via the flexible mother circuit 318.

An audio output device 316 is electrically connected to the DSP 312 via the flexible mother circuit 318. In some embodiments, the audio output device 316 comprises a speaker (coupled to an amplifier). In other embodiments, the audio output device 316 comprises an amplifier coupled to an external receiver 320 adapted for positioning within an ear of a wearer. The external receiver 320 can include an electroacoustic transducer, speaker, or loud speaker. The ear-worn device 200 may incorporate a communication device 308 coupled to the flexible mother circuit 318 and to an antenna 302 directly or indirectly via the flexible mother circuit 318. The communication device 308 can be a Bluetooth® transceiver, such as a BLE (Bluetooth® low energy) transceiver or other transceiver(s) (e.g., an IEEE 802.11 compliant device). The communication device 308 can be configured to communicate with one or more external devices, such as those discussed previously, in accordance with various embodiments. In various embodiments, the communication device 308 can be configured to communicate with an external visual display device such as a smart phone, a video display screen, a tablet, a computer, a television, a virtual or augmented reality, a hologram, or the like.

In various embodiments, the ear-worn device 200 can also include a control circuit 322 and a memory storage device 324. The control circuit 322 can be in electrical communication with other components of the device. The control circuit 322 can execute various operations, such as those described herein. The control circuit 322 can include various components including, but not limited to, a microprocessor, a microcontroller, an FPGA (field-programmable gate array) processing device, an ASIC (application specific integrated circuit), or the like. The memory storage device 324 can include both volatile and non-volatile memory. The memory storage device 324 can include ROM, RAM, flash memory, EEPROM, SSD devices, NAND chips, and the like. The memory storage device 324 can be used to store data from sensors as described herein and/or processed data generated using data from sensors as described herein.

Figure 4:
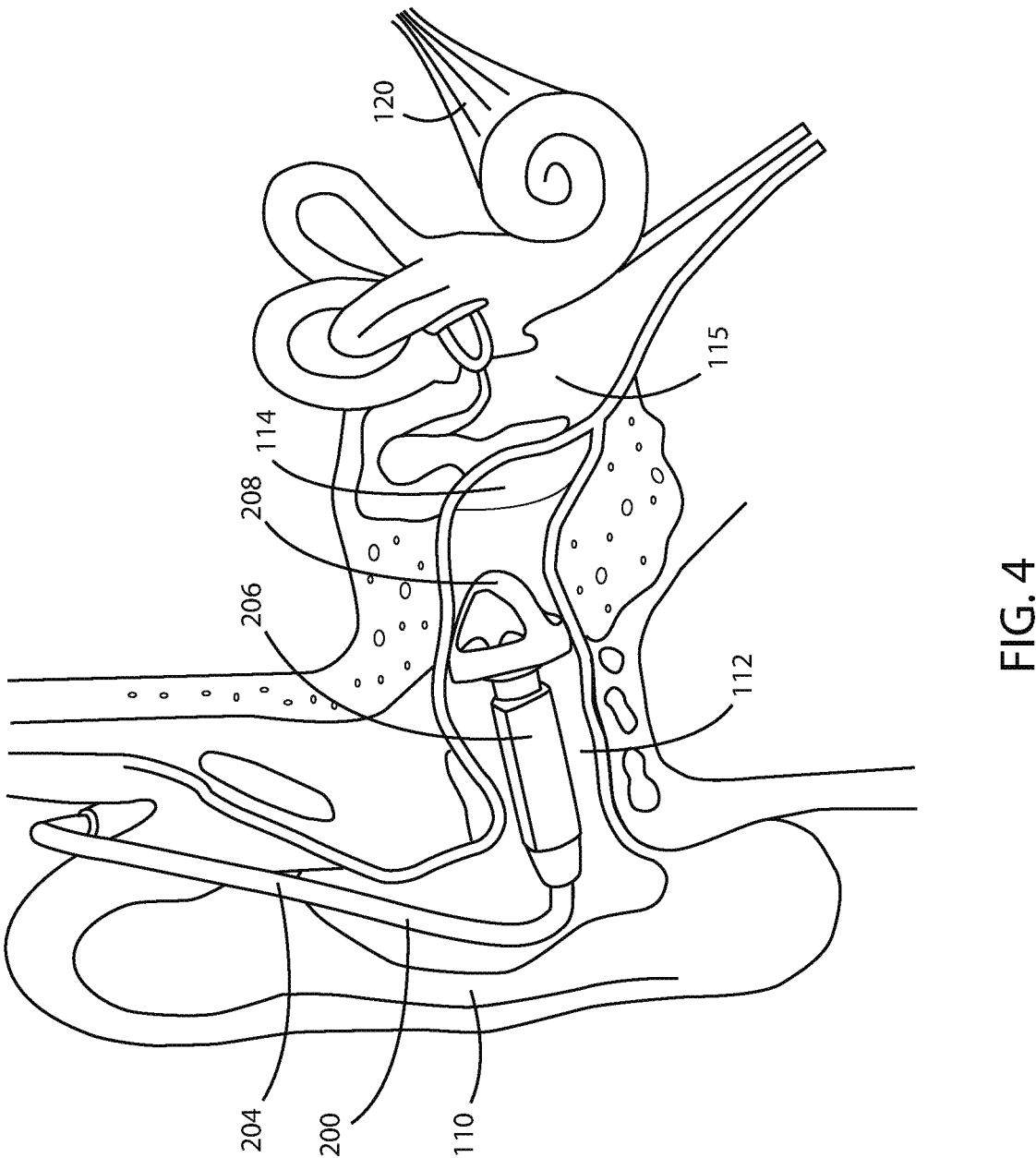
FIG. 4 is a schematic view of an ear-worn device disposed within the ear of a subject in accordance with various embodiments herein.

As mentioned regarding FIG. 2, the ear-worn device 200 shown in FIG. 2 is a receiver-in-canal type device and thus the receiver is designed to be placed within the ear canal. Referring now to FIG. 4, a schematic view is shown of an ear-worn device disposed within the ear of a subject in accordance with various embodiments herein. In this view, the receiver 206 and the earbud 208 are both within the ear canal 112, but do not directly contact the tympanic membrane 114. The hearing device housing is mostly obscured in this view behind the pinna 110, but it can be seen that the cable 204 passes over the top of the pinna 110 and down to the entrance to the ear canal 112.

Figure 5:
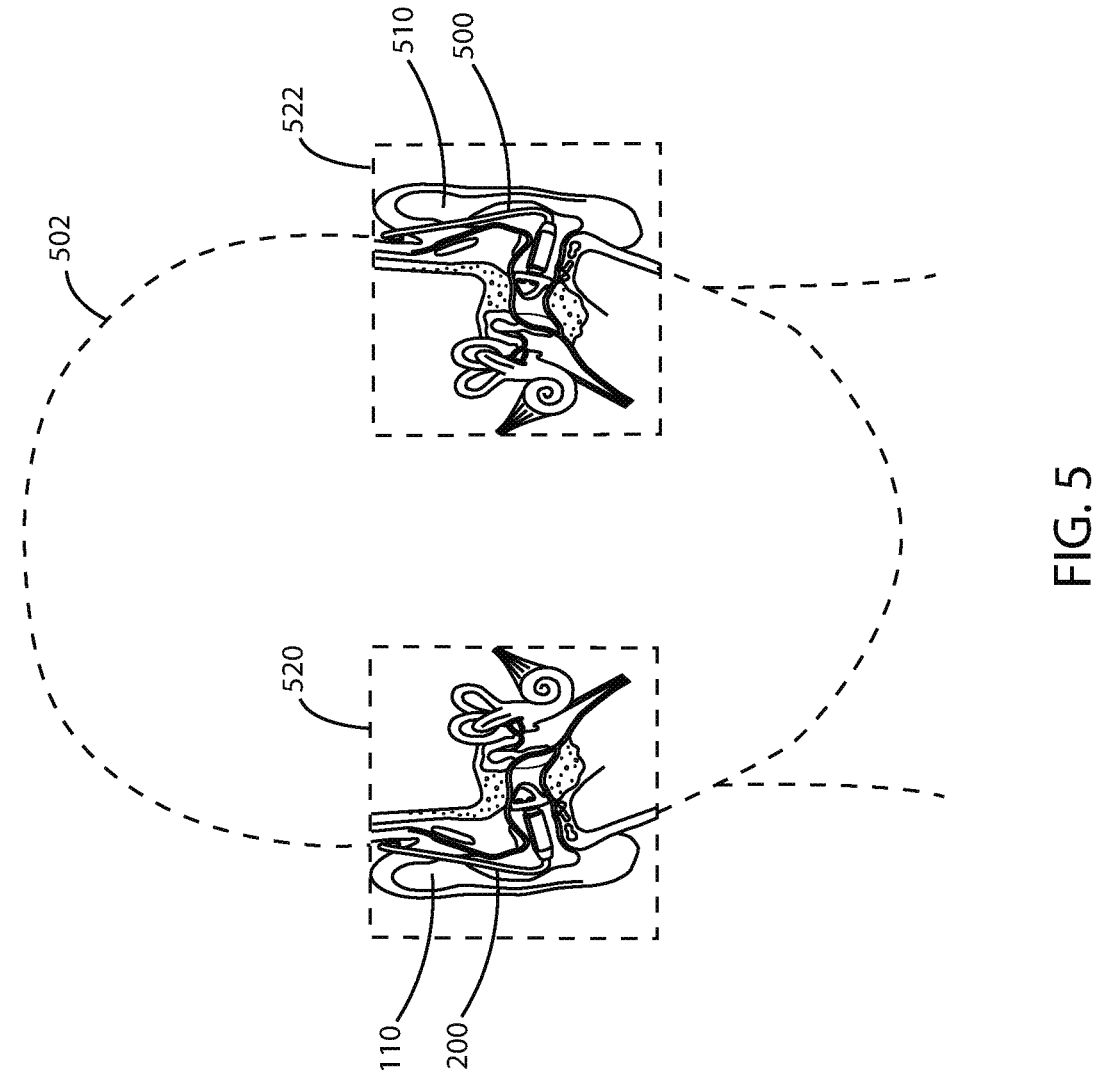
FIG. 5 is a schematic view of a pair of ear-worn devices disposed within the ear of a subject in accordance with various embodiments herein.

Referring now to FIG. 5, a schematic view is shown of a pair of ear-worn devices 200, 500 disposed within the ear of a subject 502 in accordance with various embodiments herein. FIG. 5 further shows a portion of the right side 520 of the vestibular system and a portion of the left side 522 of the vestibular system. The first ear-worn device 200 is worn about the right side pinna 110 (right side of the device wearer) and the second ear-worn device 500 is worn about the left side pinna 510.

Some embodiments herein may only use a single ear-worn device. The single ear-worn device can be used to provide stimulation (excitatory or inhibitory) such as caloric stimulation, nerve stimulation, auditory stimulation, electromagnetic field/radiation stimulation, optical stimulation, and the like. However, in various embodiments, two ear-worn devices are used and can provide differential stimulation to the left side 522 of the vestibular system and the right side 520 of the vestibular system. The two ear-worn devices 200, 500 can be used to provide differential stimulation (excitatory or inhibitory) such as differential caloric stimulation, differential nerve stimulation, differential auditory stimulation, differential electromagnetic field stimulation, differential optical stimulation, and the like. Exemplary aspects of stimulation are described in greater detail below.

In accordance with various embodiments herein, the ear-worn device and/or the system can track movement of the subject's eyes using one or more of a camera, an EOG (electrooculogram) sensor, a VOG sensor, or another device. Movement of the subject's eyes can be used to identify events such as an episode of nystagmus. Movement of the subject's eyes can also be used to identify a predicted location of a lesion, such as a lesion being present on the right or left sides of the vestibular system and/or being present within specific canals of the inner ear, etc.

Figure 6:
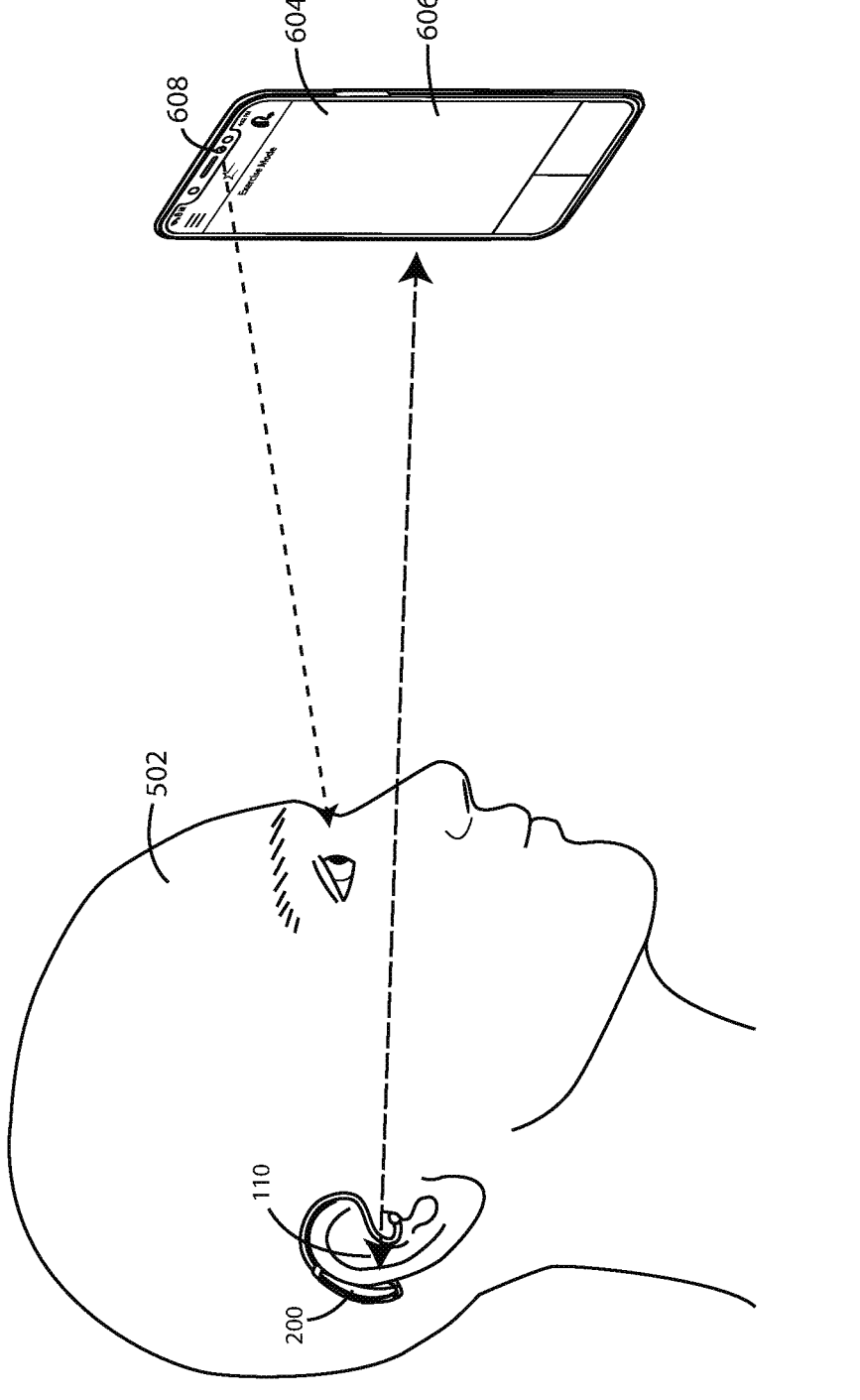
FIG. 6 is a schematic view of device wearer interfacing with an external device in accordance with various embodiments herein.

Referring now to FIG. 6, a schematic view is shown of device wearer 502 interfacing with an external device 604 in accordance with various embodiments herein. The external visual display device 604 can include a display screen 606 and a camera 608. In some embodiments, the display screen 606 can be a touch screen. The display screen 606 can display various pieces of information to the subject 502 including, but not limited to, instructions for procedures to follow, visual feedback, a target or icon for the subject to focus their gaze on, information regarding the progress of the subject 502 through a particular set of procedures, or the like.

The camera 608 can be positioned to face toward the subject 502 (in some embodiments, the camera could also be facing the display, with the subject between the camera and the display screen—using the display itself as a spatial reference). The camera 608 can be used to capture an image or images of the subject's 502 eyes. In some embodiments, the camera 608 can be used to capture image(s) including the positioning of subject's 502 face, pupil, iris, and/or sclera. Such information can be used to calculate angle, speed and direction of nystagmus, and/or to determine standard measures of nystagmus such as those described below. However, it will be appreciated, that data regarding eye movement gathered in any manner including by way of other techniques described herein can also be used to calculate angle, speed and direction of nystagmus, and/or to determine standard measures of nystagmus.

Figure 7:
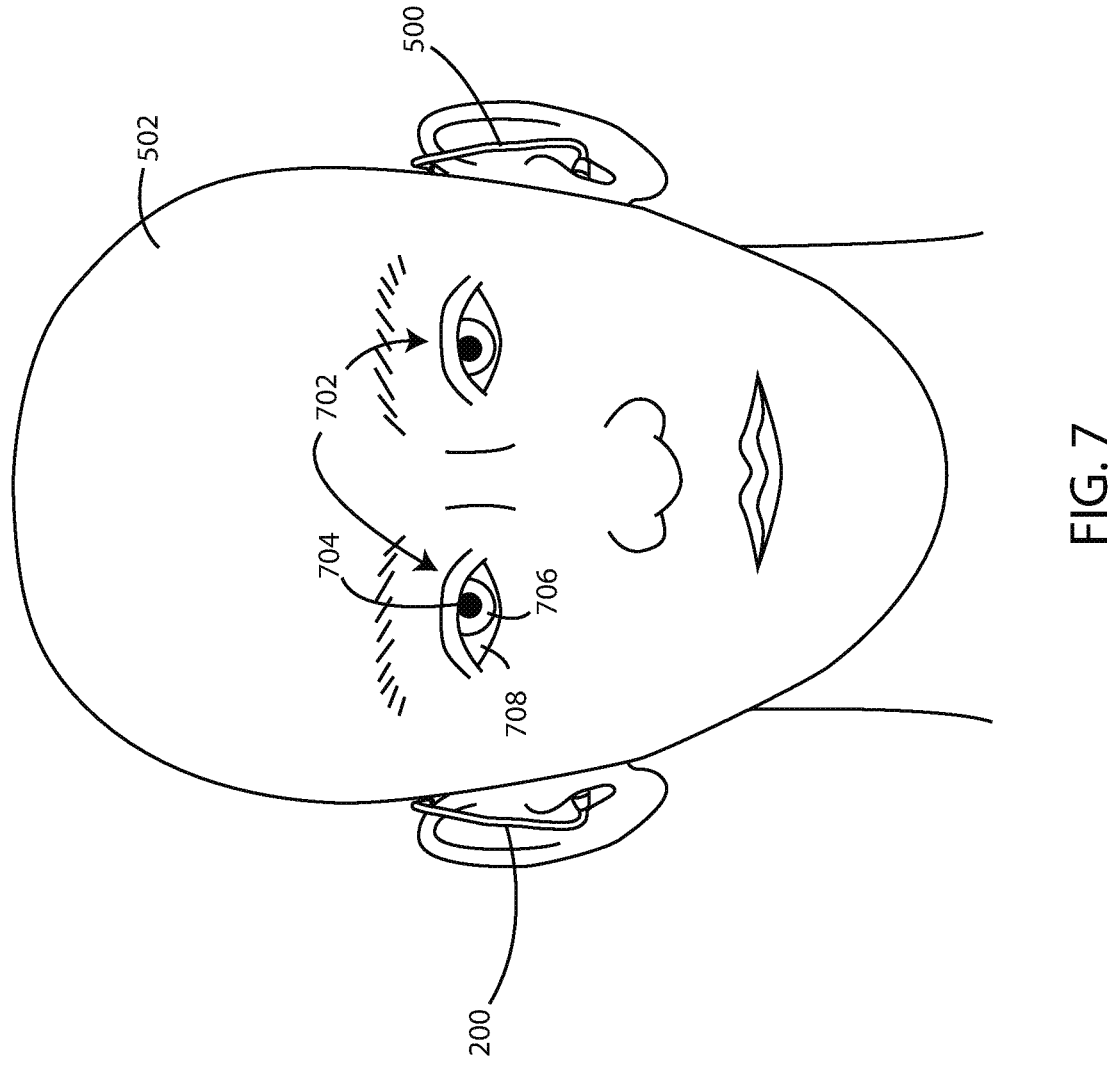
FIG. 7 is a schematic view of a pair of ear-worn devices disposed within the ear of a subject in accordance with various embodiments herein.

Referring now to FIG. 7, a schematic frontal view is shown of a subject 502 wearing ear-worn devices 200, 500 in accordance with various embodiments herein. The subject's 502 eyes 702 include pupils 704, iris 706, and sclera 708 (or white portion). Identifying the position of these and other eye components and facial components can be used to determine the direction of gaze and/or direction the face is pointing as described above. In some embodiments, the size of the pupils 704 can be monitored using camera data to detect any changes that occur during an activity of the user.

Aspects of nystagmus detection and characterization are described in commonly-owned U.S. Publ. Pat. Appl. No. 2018/0228404, the content of which is herein incorporated by reference. In some embodiments, information from other sensors (such as an EOG sensor) can be used in combination with data from the camera to more accurately calculate the direction of the subject's face, gaze, eye movement or another aspect described herein. Aspects of EOG sensors are described in U.S. Pat. No. 9,167,356, the content of which is herein incorporated by reference in its entirety.

In various embodiments herein, distinct aspects of nystagmus can be determined. By way of example, one or more standard measures of nystagmus such as fast phase velocity, slow phase velocity, direction of nystagmus beating, rotary nystagmus, directional preponderance, and gaze angle can be determined. In various embodiments, two or more of fast phase velocity, slow phase velocity, direction of nystagmus beating, rotary nystagmus, directional preponderance, and gaze angle can be determined. In various embodiments, three or more of fast phase velocity, slow phase velocity, direction of nystagmus beating, rotary nystagmus, directional preponderance, and gaze angle can be determined.

The direction of nystagmus can be defined by the direction of its quick phase (e.g. a right-beating nystagmus is characterized by a rightward-moving quick phase, and a left-beating nystagmus by a leftward-moving quick phase). In various embodiments, the lateral distribution of the equilibrium disorder and/or the likely location of a lesion can be estimated based on evaluating the elements of the observed nystagmus event. In some embodiments, observations of eye movement relative to head motion may assist the system to predict a likely location of lesion. In some embodiments, observations of eye movement, in response to stimulation of one or both sides, may assist the system to predict a likely location of lesion. Methods of tracking eye movement and head movement are described in U.S. Publ. Pat. Appl. No. 2018/0317837, the content of which is herein incorporated by reference. A reduction in input from a left-sided vestibular lesion, for instance, produces a leftward bias, which then induces a corrective saccade away from the side of the lesion. Thus, a left-sided lesion produces leftward slow phases and right jerk nystagmus. Similarly, a reduction in input from a right-sided vestibular lesion, for instance, produces a rightward bias, which then induces a corrective saccade away from the side of the lesion. Thus, a right-sided lesion produces rightward slow phases and left jerk nystagmus.

The three semicircular canals of the inner ear are approximately aligned with the movement directions of the extraocular muscles. Thus, nystagmus that follows a specific canal plane often results from a peripheral lesion of that same canal, while nystagmus in other directions is likely of central origin. As an example, pure vertical or torsional nystagmus is likely not of peripheral vestibular origin, but more likely has a central cause. A peripheral cause also leaves fixation suppression largely intact, since central fixation mechanisms are spared. Cross-coupling (e.g., vertical nystagmus after horizontal head motions) also indicates a central cause. Therefore, evaluation of the directionality of the nystagmus along with other features thereof allows the system herein to estimate a site of a lesion.

In some embodiments herein, information regarding a predicted location of a lesion and/or predicted side of the source of an equilibrium disorder allows for differential stimulation of the right and left side of the vestibular system herein. For example, if it is determined that the device wearer has an equilibrium disorder originating on their left side, then the system can stimulate (solely or differentially) the left side to address this issue. In some scenarios, the directionality may be reversed in that if the system determines that the device wearer has an equilibrium disorder originating on their left side, then the system can stimulate the right side to address the issue.

Many stimulation schemes are envisioned. In some embodiments, one side can be stimulated and the other side can remain unstimulated. In some embodiments, both sides can be stimulated, but one side can be stimulated at a higher level of intensity and/or differently. In some embodiments, one side can be stimulated in an excitatory manner and the other side can be stimulated in an inhibitory manner. In some embodiments, one side can be stimulated about 5, 10, 20, 30, 40, 50, 75, 100, 150, 200, 300, 400, 500, 1000, 2000, or 3000 percent more intensely, or an amount falling within a range between any of the foregoing. In some embodiments, the intensity of stimulation for one side may be adapted differently, over time, when compared to the intensity of stimulation applied to the other side.

In various embodiments herein, characteristics of an equilibrium disorder can be determined including, but not limited to, the site of a lesion (as described above), the device wearer's perceived head position versus actual head position, and the device wearer's perceived head movement versus actual head movement. For example, actual head position and head movement can be determined based on sensors herein, such as described in FIGS. 9-11. Perceived head position and head movement can also be determined. For example, in various embodiments herein, eye movements can be used to determine perceived head movement (such as based on the vestibular ocular reflex—VOR) as well as perceived head position (such as based on a calculated ending point of perceived head movement). Thus, perceived head position can be compared to actual head position and perceived head movement can be compared to actual head movement.

Gait

In various embodiments, a method of improving gait and/or balance of a device wearer is included herein. The method can include monitoring device wearer movement with a movement sensor, identifying a movement pattern consistent with sustained cyclical strides, evaluating the gait and/or balance of the device wearer by analyzing data from the movement sensor, and applying auditory stimulation and/or auditory feedback to at least one of the right or left ear using an ear-worn device.

In accordance with various embodiments herein, the device wearer's gait and/or balance can be evaluated. Gait analysis can include the evaluation of body movements, body mechanics, and the activity of the muscles during human motion generally and, in particular, during movements such as walking or running. Specific parameters of gait analysis can include, but are not limited to, step length (right, left), stride length, stride length to lower extremity length ratio, horizontal dimension of stride, base of support, stride cycle element analysis, frequency (cadence), speed, dynamic base, progression line, foot angle, hip angle, and the like.

Figure 8:
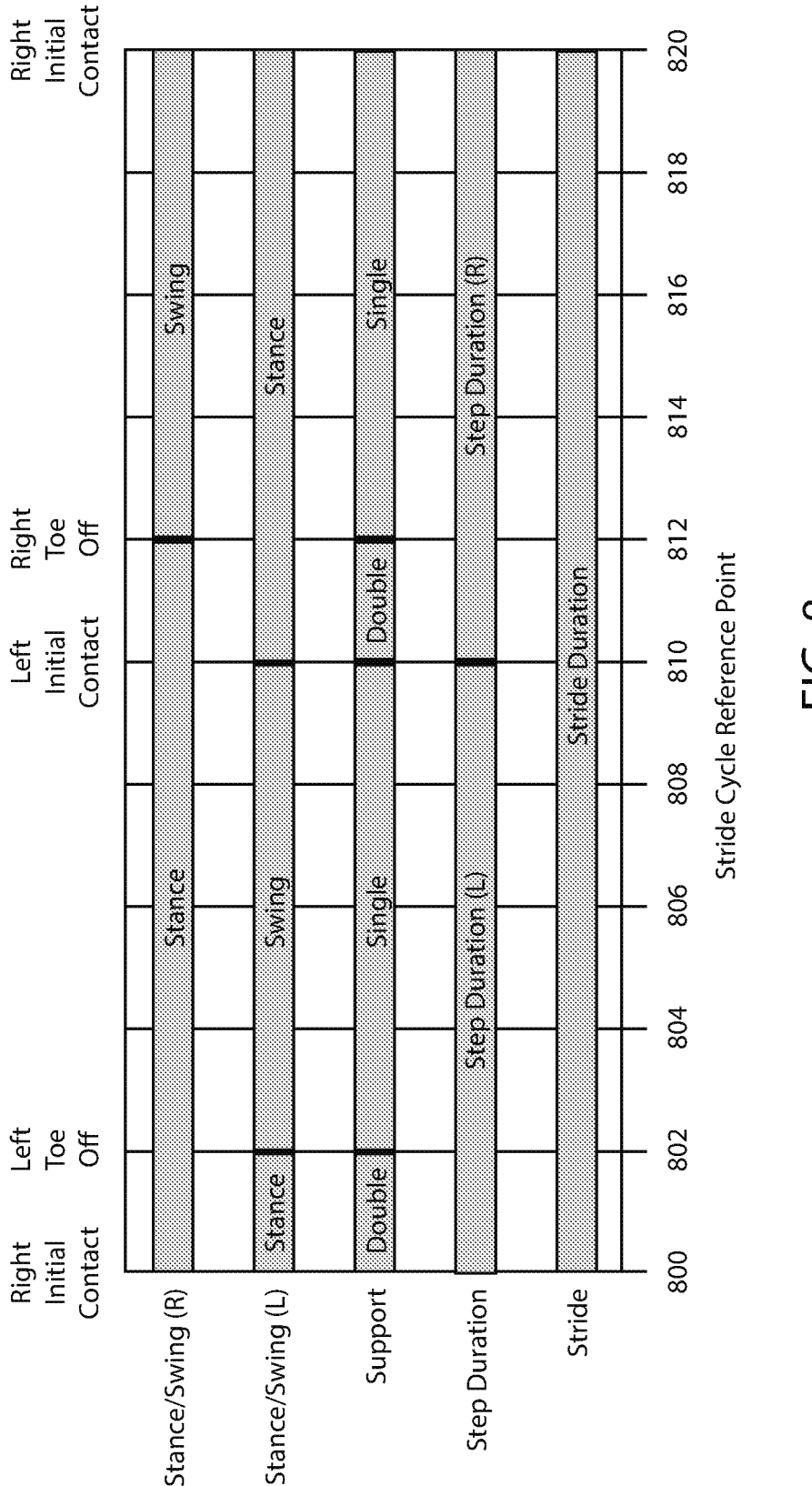
FIG. 8 is a diagram of events occurring during strides of a device wearer for gait analysis in accordance with various embodiments herein.

It will be appreciated that a device wearer's stride can be broken down into many different sub-elements for purposes of gait analysis herein. Referring now to FIG. 8, a diagram is shown of events occurring during strides of a device wearer for gait analysis in accordance with various embodiments herein.

At reference point 800, the right foot makes initial contact with the ground and both the right leg and the left leg are in a stance. Support is provided by both legs (e.g., double) beginning at this time.

At reference point 802, the left toe leaves the ground and the left leg enters a swing while the right leg is in a stance. Support is provided by only the right leg (e.g., single) beginning at this time. At reference points 804, 806, and 808 the swing of the left leg continues.

At reference point 810, the left foot makes initial contact with the ground and both the right leg and the left leg are in a stance. Support is provided by both legs beginning at this time.

At reference point 812, the right toe leaves the ground and the right leg enters a swing while the left leg is in a stance. Support is provided by only the left leg (e.g., single) beginning at this time. At reference points 814, 816, and 818 the swing of the right leg continues. Reference point 820 marks the conclusion of the stride cycle whereupon if the device wearer continues to walk the cycle will repeat beginning at reference point 800.

In accordance with embodiments herein, one or more of an IMU unit and a microphone herein can detect movements and/or vibrations in order to identify what stage of the stride cycle the device wearer is currently in along with frequencies and time associated with the same. By way of example, reference points 800 and 810 involve the right and left feet, respectively, making initial contact with the ground. The biomechanics associated with such feet/ground contact results in characteristic acoustic and inertial changes that can be detected by one or more microphones and/or accelerometers (or other component) of an IMU, either alone or in combination. In some embodiments, characteristics of feet/ground contact can include a signal intensity. In some embodiments, characteristics of feet/ground contact can include a time interval. In some embodiments, characteristics of feet/ground contact can include an angular position of one or more parts of the body. For example, as one leg swings forward (e.g., starting at reference point 802 and ending at reference point 810 for the left leg and starting at reference point 812 and ending at reference point 820 for the right leg) support by the other leg involves a characteristic vertical motion at a relatively low frequency that can be detected by a component of the IMU.

Characteristic medio-lateral axis movement can also be detected by the IMU during different phases of the stride cycle allowing each point to be identified along with timing of the same. By way of example, a limping gait can be reflected as unequal swing durations between each leg and this type of abnormal gait can be detected by the system. As another example, a shuffling-type gait can be reflected as a measurable variability in the timing of the different phases of the stride cycle that crosses a threshold value of variability (the threshold value either being pre-selected and programmed into the device or reflecting a statistical measure of deviation from an average for the specific individual as calculated over a look-back period or during a previous calibration period or event). A shuffling-type gait can also be detected using acoustic information obtained from one or more microphones.

In addition, by combining the information content provided by signals associated with directional movement in the horizontal plane (as can be measured by the IMU, microphone, or geolocation-type sensors) with that provided by stride cycle analysis as detailed above, aspects such as step length (right, left) and stride length can be calculated. These values can also be subjected to analysis to determine various statistics, e.g., absolute values (average right step length, average left step length, average stride length) as well as ratios of the same (ratio of average right step length vs. average left step length) and measures of variability in the same, and the like. In various embodiments, the system can be configured to evaluate these measures by comparison with a threshold value or confidence interval for significance, wherein the threshold value can be pre-selected and programmed into the device or reflect a statistical measure of deviation based on a statistically measured value for the specific individual as calculated over a look-back period or during a previous calibration period or event. For reference, typical pacing of steps is shown below in Table 1.

TABLE 1

| Pace | Steps/Minute | Hertz |
| --- | --- | --- |
| Slow | <60 | <1 |
| Medium | ≥60 and ≤120 | ≥1 and ≤2 |
| Fast | >120 | >2 |

In various embodiments herein, the system can further evaluate progression line of locomotion as a component of gait analysis. Progression line reflects deviations from a predominant direction of locomotion that may occur non-volitionally. By way of example, when walking in a particular direction, movements along a medio-lateral axis (as can be measured by the IMU or other sensors herein) can contribute to variation in the progression line of the device wearer. One approach to measuring variation in progression line is to take the absolute magnitude of movement along a medio-lateral axis and divide by a fixed distance of travel in the predominant movement direction (walking/running direction). Various approaches can be used for measuring variation in progression line.

Freezing of gait (FoG) is a particular abnormal gait feature that is commonly associated with early Parkinson's disease. FoG is believed to be due to a loss of postural reflexes and is defined as an onset of not being able to start stepping forward, with no apparent cause. FoG can be exacerbated by stress, distraction, or increased cognitive loads (such as when navigating obstacles along a walkway or when performing multiple tasks simultaneously, e.g., talking while walking). Onset of FoG may be at the beginning of a volitional sequence of motions (such as when first starting to walk in a particular direction) or may occur during a volitional sequence of motions (such as when walking but then hearing someone call their name or another type of audible sound capturing their attention).

In accordance with various embodiments herein, FoG can be detected by analyzing the signals from an IMU, alone or in combination. In some embodiments, an operatively connected brain sensor may assist with the detection or prediction of FoG behaviors. By way of example, the Moore-Bächlin FoG Algorithm (MBFA) can be used to identify an FoG episode. In various embodiments, a machine learning approach based on Support Vector Machines (SVM) can be used to identify FoG episodes using the signals from the IMU as input. In other embodiments, various different machine learning techniques can be used to predict episodes of a wearer's FoG or conditions that may result in a wearer's FoG.

Postural control consists of both postural steadiness associated with the ability to maintain balance during quiet standing and postural stability that is associated with the response to applied external stimuli and volitional movements. Postural sway describes horizontal movements of an individual around the subject's center of gravity (COG) over their base of support. Aspects of postural sway can be observed during quiet standing as well as during volitions movements such as walking. Postural sway can include anterior-posterior axis motion, medial-lateral axis motion, and combinations thereof in the horizontal plane. Postural sway can be sensed and/or tracked in accordance with various embodiments herein.

Figure 9:
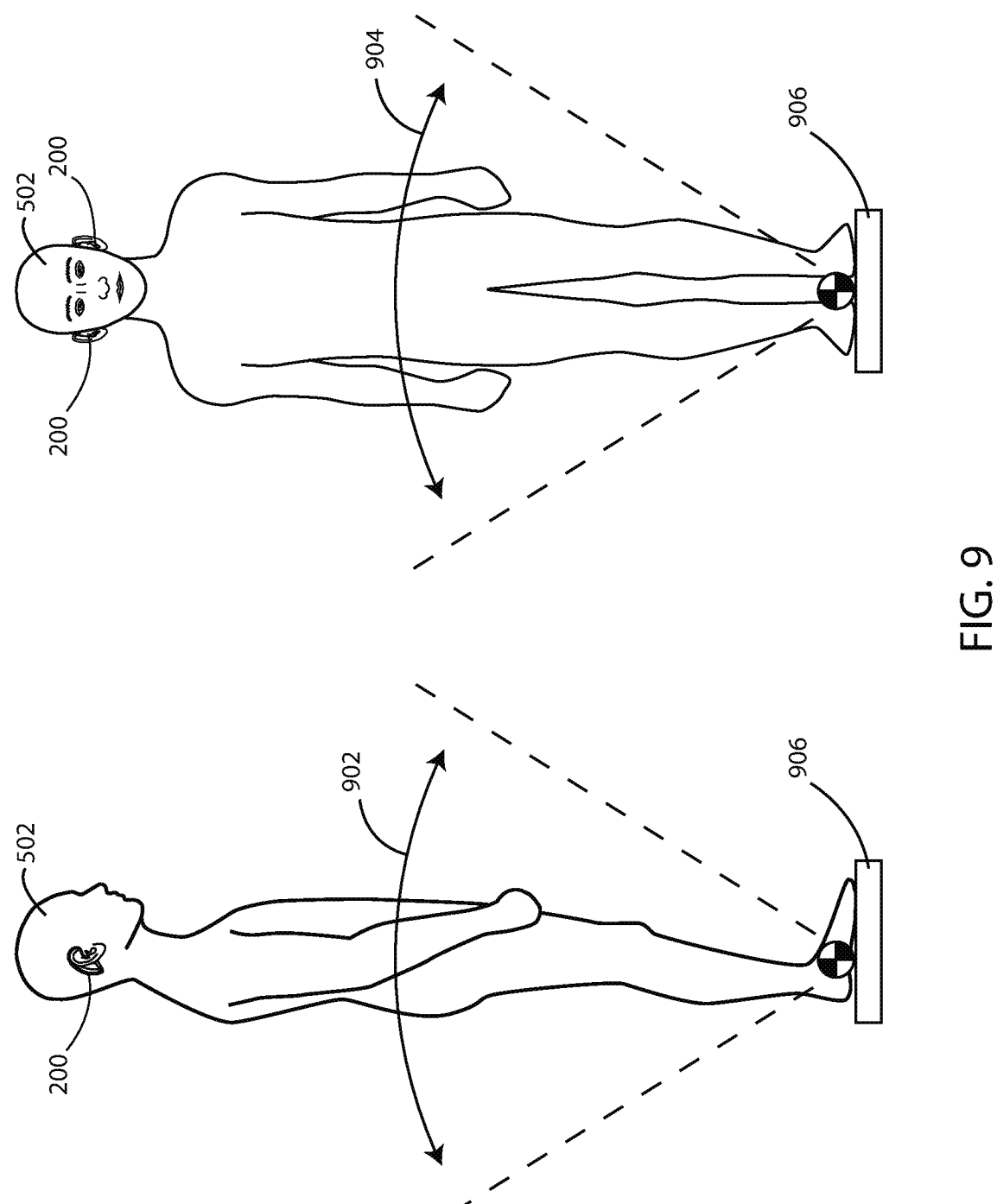
FIG. 9 is a schematic view of postural sway of a device wearer wearing a pair of ear-worn devices disposed within the ear of a subject in accordance with various embodiments herein.

Referring now to FIG. 9, a schematic view is shown of postural sway of a device wearer 502 wearing a pair of ear-worn devices 200, 500 disposed within the ear of a subject in accordance with various embodiments herein. Postural sway can include anterior-posterior axis motion 902, medial-lateral axis motion 904, as well as combinations thereof. It will be appreciated that movement contributing to sway can include movement initiated at any point of the body including at the level of the feet and ankles, movement at the level of the knees, hips, back, neck, head, and the like.

Parameters of postural sway that can be sensed herein can include, but are not limited to, sway size (distance), sway velocity, sway frequency, slow sway components (0.1 to 0.5 Hz), fast sway components (0.5 to 1 Hz), and the like. By way of example, an IMU unit herein (such as associated with the ear-worn device) can detect movements and/or vibrations in order to identify what stage of the stride cycle the device wearer is currently in along with frequencies and time associated with the same. The vestibulocollic reflex (VCR) acts to stabilize the head (such as by acting upon muscles in the neck to counter movement sensed by otoliths or semicircular canals), but individuals with abnormal sway may still exhibit a measurable sway of the head. While not intending to be bound by theory, detection of sway in the head is highly probative of dysfunction impacting balance and stability. Therefore, in some embodiments, detection of sway in the head is prioritized by the system.

In some embodiments, detection of sway can be performed automatically by the system without the volitional participation of the device wearer. In some cases, the system can measure sway regardless of the current activity of the device wearer. However, in other embodiments, the system can wait until e.g., a standing state is detected (which could occur as the device wearer is standing in line or otherwise standing, but not moving within the horizontal plane), a walking state is detected, or the like.

In some embodiments, the device can provide instructions for the device wearer to follow, such as "please stand still" (explicitly or implicitly) provided. For example, instructions can be provided directly from the ear-worn device through audible or tactile channels. In some embodiments, instructions can be provided from an external device through one or more of an audible, visual, or tactile modality.

In some cases, the movements to track, measure, or monitor postural sway can be performed with sensors associated with the ear-worn devices alone. However, in other cases, sensors associated with other devices can be used in addition to, or in place of, the sensors associated with the ear-worn devices (in which case signals from a different device relevant to postural sway can be sent to the ear-worn devices or a different device). By way of example, in some embodiments, a pressure-plate device 906 can be used to identify movement or weight bearing/transfer related to postural sway. The pressure-plate device 906 can include one or more load cells or other types of related sensors such as pressure-sensors and the like to detect sway and aspects thereof. In some embodiments, elements of a pressure-plate device 906 can be embedded within a surface, such as a floor.

Figure 10:
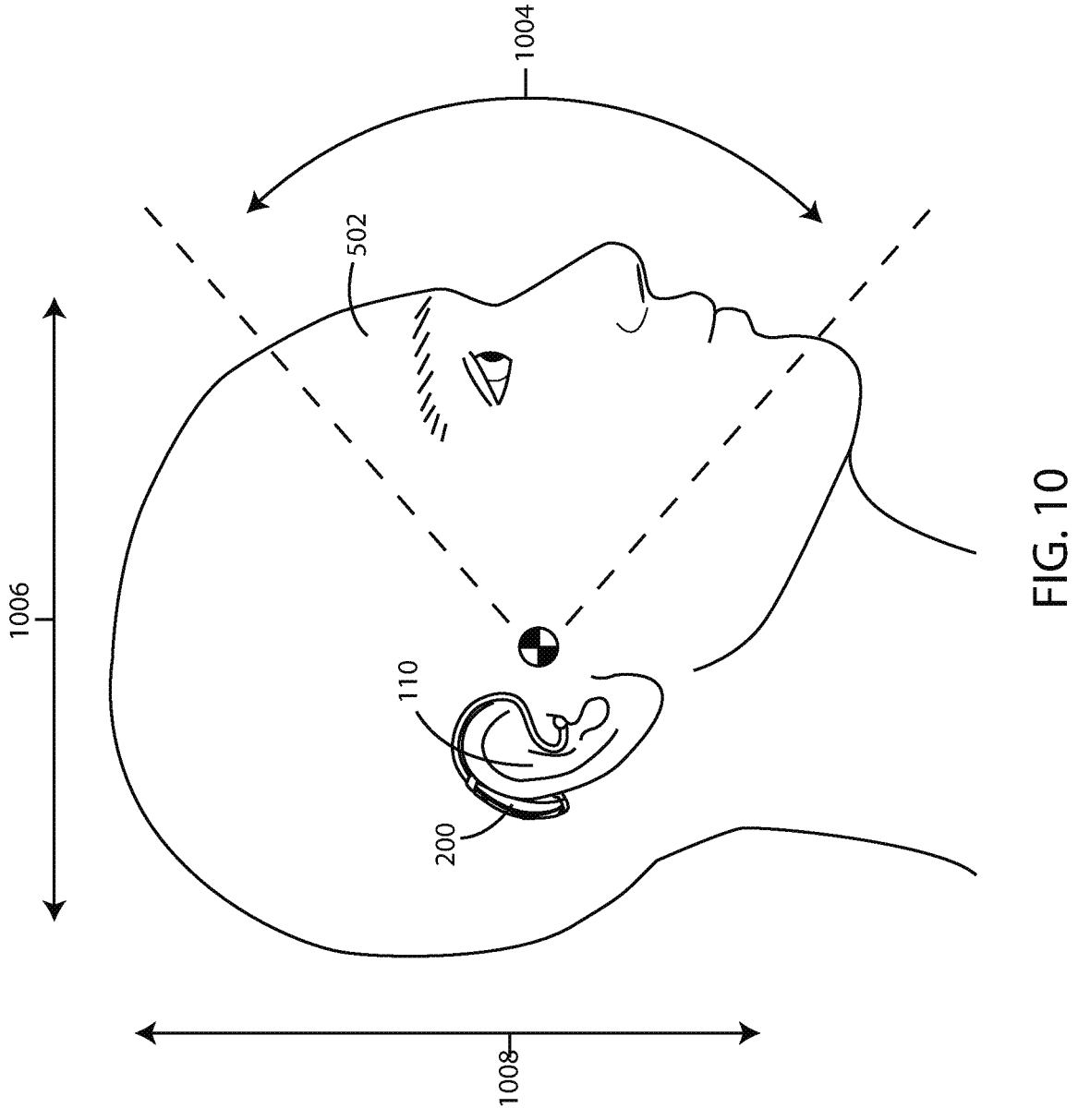
FIG. 10 is a schematic side view of a subject wearing an ear-worn device in accordance with various embodiments herein.

Ear-worn devices herein can include sensors (such as part of a sensor package) to detect movements of the subject wearing the ear-worn device. Amongst other things, ear-worn device herein can specifically detect head movements of the subject wearing the ear-worn device. Referring now to FIG. 10, a schematic side view is shown of a subject 502 wearing an ear-worn device 200 in accordance with various embodiments herein. For example, head/body movements detected can include rotational movements 1004 in the vertical plane, forward/back movements 1006, up/down movements 1008, and the like. Sensors herein, including IMU sensors or IMU-associated sensors, can be used to measure movements 1004, 1006, 1008, and the like.

Figure 11:
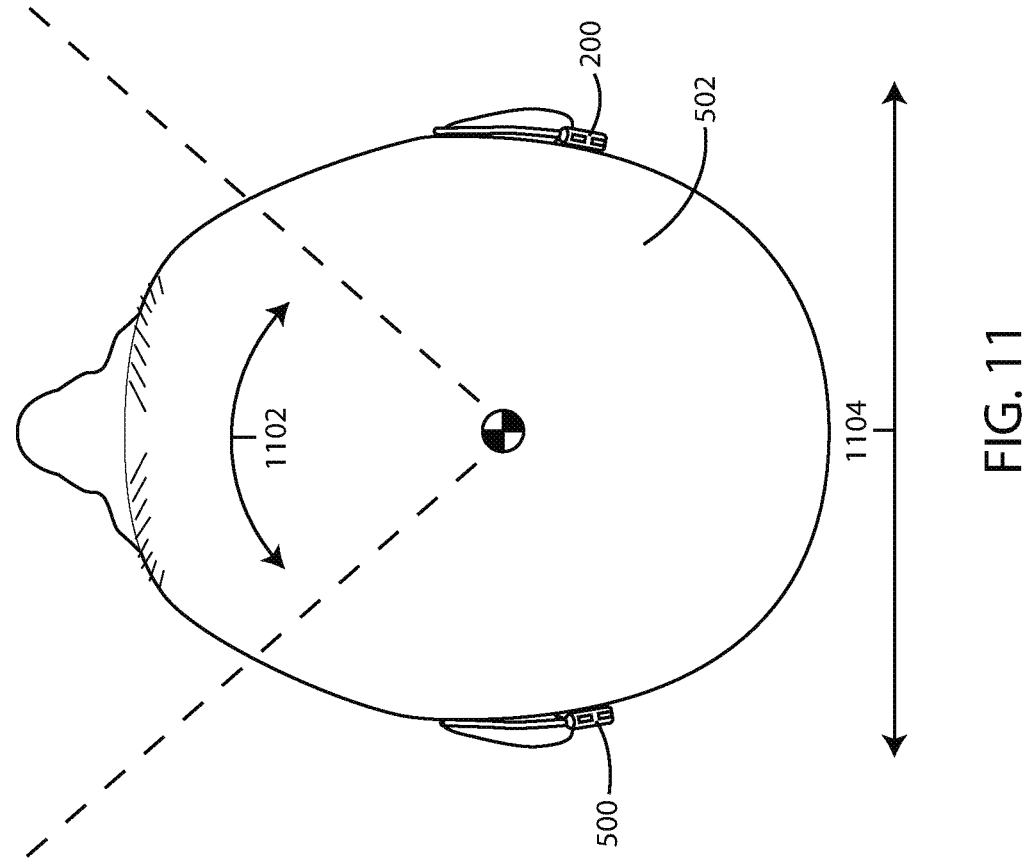
FIG. 11 is a schematic top view of a subject wearing ear-worn devices in accordance with various embodiments herein.

Referring now to FIG. 11, a schematic top view is shown of a subject 502 wearing ear-worn devices 200, 500 in accordance with various embodiments herein. Movements detected can rotational movements 1102 in the horizontal plane, side-to-side movements 1104, and the like. Sensors herein, including IMU sensors or IMU-associated sensors, can be used to measure movements 1102, 1104, and the like.

In various embodiments herein, a method of improving gait and/or balance of a device wearer is included. The method can include monitoring device wearer movement with a movement sensor, identifying a movement pattern consistent with sustained cyclical strides, evaluating the gait and/or balance of the device wearer by analyzing data from the movement sensor, and applying auditory stimulation and/or auditory feedback to at least one of the right or left ear using an ear-worn device. In some embodiments, one or more acoustic sensors or microphones can be used to identify a movement pattern. In some embodiments, one or more acoustic sensors can be used in combination with one or more other motion sensors to detect a movement pattern.

Auditory stimulation can be as described elsewhere herein. Auditory feedback can specifically include sound within the detectable frequency range for humans (e.g., between 20 Hz and 20,000 Hz). In some embodiments, the sound may include words such as "left", "right", or "step" and "step". In some embodiments, the sound may include metronomic beats. In some embodiments, the sound may include rhythmic changes in volume and/or frequency. In some embodiments, the sound may include music or fractal sounds that may be manipulated in degrees of tempo or other aspects relating to a beat, such as beat volume and/or frequency.

Auditory feedback can be timed to provide pacing for foot contact (right or left) in accordance with the stride cycle discussed above, or pacing for any other events described therein. Auditory feedback can be timed to reflect a recent consistent rhythm or to reflect a preselected or dynamically selected desired pace. A recent consistent rhythm can be a rhythm observed by the system for the device wearer at a previous time point and/or the most recent consistent rhythm observed by the system (with the prior 5, 10, 30, 60, 120, 180, 360, 720, 1080, 2160 seconds or more). In some embodiments, auditory stimulation or auditory feedback can be provided at a frequency of about 0.5 Hz to 3 Hz, or about 0.75 Hz to 2.5 Hz, or about 1 Hz to 2 Hz. In some cases, auditory feedback can be timed to occur at the specific desired time of an event of the stride cycle or, in some cases, slightly before, such as 1, 10, 20, 30, 40, 50, 60, 75, 100, 200, 250, 300, 500, or 1000 milliseconds before (or an amount falling within a range between any of the foregoing).

In various embodiments, auditory feedback can specifically include spoken word feedback to the device wearer. In some embodiments, the spoken word feedback to the device wearer can be in regard to the identified movement pattern (e.g., "you are walking faster now", "keep walking at this pace", "try to walk at a faster pace", etc.). In some embodiments, the spoken word feedback to the device wearer can include or relate to recommended changes to the identified movement pattern.

As referenced above, FoG can occur after the subject hears their name or their attention is otherwise drawn by a sound. Similarly, subject may also stop walking/running when they or another person starts to speak. This phenomenon is known as "stops walking when talking". In various embodiments herein, the system can specifically monitor for movement changes during the spoken word feedback indicative of a stops walking when talking response. In various embodiments, signals from a microphone or similar device can be monitored in conjunction with signals from the IMU or other sensor in order to identify an episode of "stops walking when talking". For example, when sound indicative of speech is detected, then the device or system can also evaluate signals from the IMU or other sensor in order to detect an occurrence of "stops walking when talking".

In some embodiments, the system can cease the auditory stimulation when the movement pattern consistent with sustained cyclical strides ceases. In some embodiments, monitoring device wearer movement with one or more of a movement sensor and/or microphone is performed by an ear worn device. In some embodiments, identifying a movement pattern consistent with sustained cyclical strides is performed by an ear worn device. In some embodiments, evaluating the gait and/or balance of the device wearer by analyzing data from the movement sensor is performed by an ear worn device.

In various embodiments, a method of improving gait and/or balance of an ear-worn device wearer is included herein. The method can include monitoring device wearer movement with an ear-worn device, such as those described herein. The method can also include applying cyclical auditory stimulation or feedback to at least one of the right or left ear at a cyclical frequency using the ear-worn device, wherein the cyclical frequency equals an ambulatory pace. Auditory stimulation and feedback can be as described elsewhere herein.

In some embodiments, auditory stimulation or auditory feedback can be provided at a frequency of about 0.5 Hz to 3 Hz, or about 0.75 Hz to 2.5 Hz, or about 1 Hz to 2 Hz. In some embodiments, auditory stimulation or auditory feedback can be provided at a pace that is faster than the determined sustained cyclical stride pace when the determined sustained cyclical stride pace is below a threshold value. The threshold value can be predetermined or can be adaptively determined for the specific device wearer. In some embodiments, auditory stimulation or auditory feedback can be provided at a pace that is slower than the determined sustained cyclical stride pace when the determined sustained cyclical stride pace is above a threshold value.

In some embodiments, devices herein can be configured to analyze data from the movement sensor to determine a sustained cyclical stride pace of the device wearer. In some embodiments, identifying a movement pattern consistent with sustained cyclical strides includes identifying a movement pattern consistent with sustained cyclical strides that is sustained for at least 1, 2, 3, 4, 5, 7, 10, 15, 20, 30, or 60 seconds, or an amount of time falling within a range between any of the foregoing. In various embodiments, the determined sustained cyclical stride pace can be stored along with a timestamp. In various embodiments, the system can further calculate a trend in the determined sustained cyclical stride pace over time.

In accordance with various embodiments herein, the system can send an alert to a third party when the trend indicates a possible decompensation event. A possible decompensation event can be marked by a precipitous decline in one or more gait parameters described herein. In some embodiments, a possible decompensation event can be marked by a greater than 20 percent decline in one or more gait parameters described herein.

Stimulation

As described above, in various embodiments herein, one or more ear-worn devices can be used to provide stimulation to the device wearer. In particular, one or more ear-worn devices can be used to provide vestibular system stimulation and/or nervous system stimulation to the device wearer. For example, an ear-worn device can be used to provide stimulation to the vestibular system of the device wearer (left side, right side, or both) and/or the brainstem of the device wearer. In some embodiments, a pair of ear-worn devices can be used to provide differential (e.g., right side vs. left side) stimulation to the device wearer.

Many types of stimulation can be used herein. By way of example, stimulation can be excitatory or inhibitory. Stimulation can take the form of caloric stimulation, nerve stimulation, auditory stimulation, electromagnetic field/radiation stimulation, optical stimulation, and the like.

Stimulation can be delivered to a selected site or sites of stimulation of the device wearer. Sites of stimulation herein can include, but are not limited to, on or about the ear, the ear canal, the inner ear, adjacent nerves related to the vestibular system, the brainstem, and the like. As one specific example, the ear canal can serve as a useful site of stimulation as it can serve as a conduit to the subject's vestibular system, vestibulocochlear nerve, cranial nerve, or brainstem. In some embodiments, the site of stimulation can be at or adjacent to a distal end (innermost end) of the ear canal. In some embodiments, the site of stimulation can be at or adjacent to a proximal end (outermost end) of the ear canal. In some embodiments, the site of stimulation can be at a peripheral surface of the ear canal in between the distal and proximal ends. In some embodiments, the site of stimulation can be at or about the tympanic membrane. In some embodiments, the site of stimulation can be outside of the ear canal. In some embodiments, the site of stimulation can be on the ear itself. In some embodiments, the site of stimulation can be behind the ear. In some embodiments, the site of stimulation can be along the neck or approximate the base of the skull.

Caloric stimulation can include the application of heat or the removal of heat (e.g., cooling) from a selected site of stimulation of the device wearer. By heating or cooling the temporal bone around the canals, fluid dynamics are impacted. Cooling of the temporal bone and the fluids closest in the canal change density of the endolymph leading to fluid movement of the same. By way of example, in some head positions, cooling causes counter-clockwise movement in the right ear and warming causes clockwise movement in the right ear. In some embodiments, the amount of caloric stimulation is sufficient to raise or lower the temperature at a site of stimulation by about 0.1, 0.2, 0.3, 0.4, 0.5, 0.75, 1, 1.25, 1.5, 2, 3, 4, 5, 7, 10, 15, 20, 25, 30, or 35 degrees Celsius, or an amount falling within a range between any of the foregoing. In some embodiments, the caloric stimulation can be applied for at least about 1, 5, 10, 30, 60, 120, 180, 240, 360, 720, 1080, 2160 seconds or more, or an amount of time falling within a range between any of the foregoing. In some embodiments, the caloric stimulation(s) can be delivered as part of a stimulation cycle including "on" periods and "off" periods. In some embodiments, one side can be heated while the other is cooled. In some embodiments, one side can be heat or cooled while no caloric stimulation is applied to the other side. In some embodiments, both sides can be heated, but one side can be heated to a greater degree. In some embodiments, both sides can be cooled, but one side can be cooled to a greater degree. In some embodiments, caloric stimulation herein can be accompanied by an instruction (auditory, visual, and/or haptic) to the device wearer to move their head to a certain position prior to or during the caloric stimulation.

Nerve stimulation can include electrical stimulation of nerves, such as CN-VIII. In some embodiments, a DC current can be applied. In some embodiments, an AC current can be applied. In some embodiments, the amplitude and frequency of the applied current can be effective to achieve an excitatory or an inhibitory effect. In some embodiments, excitatory stimulation can be achieved by stimulating nerves at a frequency which promotes nerve conduction or stimulating specific nerves that cause or upregulate a particular action or response. In some embodiments, inhibitory stimulation can be achieved by stimulating nerves at a frequency which suppresses nerve conduction or stimulating specific nerves that inhibit, suppress, or otherwise downregulate a particular action or response. In some embodiments, the nerve stimulation can be applied for at least about 0.0001, 0.001, 0.01, 0.1, 0.5, 1, 5, 10, 30, 60, 120, 180, 240, 360, 720, 1080, 2160 seconds or more, or an amount of time falling within a range between any of the foregoing. In some embodiments, the nerve stimulation can be delivered as part of a stimulation cycle including "on" periods and "off" periods. Exemplary electrical stimulation frequencies can include 5, 10, 20, 30, 40, 50, 60, 70, 80, 90, 100, 120, 140, 160, or 180 Hz, or frequencies falling within a range between any of the foregoing. Other frequencies are also contemplated herein.

Auditory stimulation can include the generation of sound delivered to the device wearer. In various embodiments, the volume, frequency, frequencies, frequency band or bands can be effective to achieve an excitatory or an inhibitory effect. In some embodiments, the auditory stimulation can be applied for at least about 1, 5, 10, 30, 60, 120, 180, 240, 360, 720, 1080, 2160 seconds or more, or an amount of time falling within a range between any of the foregoing. In some embodiments, the auditory stimulation can be delivered at a frequency or frequency band within the bounds of normal human hearing (e.g., 20 to 20,000 hertz). In some embodiments, the auditory stimulation can be delivered at a frequency or frequency band outside the bounds of normal human hearing. In some embodiments, the auditory stimulation can be provided at multiple frequency bands. In some embodiments, the auditory stimulation can include sound with substantially equal volume across a broad frequency spectrum. In some embodiments, the auditory stimulation can include white noise at an intensity of at least about 60 dB SPL. In some embodiments, the auditory stimulation can include pink noise at an intensity of at least 60 dB SPL.

In some embodiments, the auditory stimulation can be delivered as part of a stimulation cycle including "on" periods and "off" periods. In some embodiments, the auditory stimulation can be delivered substantially constantly for a defined period of time. In some embodiments, auditory stimulation can be delivered substantially constantly until one or more measures of gait analysis herein achieve normal values.

Electromagnetic stimulation can include the generation of an electromagnetic field and/or electromagnetic radiation delivered to the device wearer. The frequency, frequencies, frequency band, frequency bands, waveform, amplitude, field strength, etc. can be effective to achieve an excitatory or an inhibitory effect. In some embodiments, the electromagnetic field can specifically be a magnetic field. In some embodiments, the electromagnetic field can be from about 1 to 30 kV/m in strength at a frequency of about 10, 20, 30, 40, 50, 60, 70, 80, 90, or 100 Hz (or falling within a range between any of the foregoing). In some embodiments, electromagnetic radiation can be applied at frequencies within the short radio wave band, long radio wave band, microwave band, and the like. In some embodiments, electromagnetic radiation can be applied at a power of 0.01, 0.1, 0.5, 1, 1.5, 2, 3, 4, 5, 7.5, 10, 20, 30, 40, or 50 Watts or more or an amount of power falling within a range between any of the foregoing.

In some embodiments, the electromagnetic stimulation can be applied for at least about 0.0001, 0.001, 0.01, 0.1, 0.5, 1, 5, 10, 30, 60, 120, 180, 240, 360, 720, 1080, 2160 seconds or more, or an amount of time falling within a range between any of the foregoing. In some embodiments, the electromagnetic field/radiation stimulation can be delivered as part of a stimulation cycle including "on" periods and "off" periods.

Optical stimulation (as a specific form of electromagnetic radiation stimulation) can include the generation of light that is delivered to the device wearer. The frequency, frequencies, frequency band, frequency bands, and intensity can be effective to achieve an excitatory or inhibitory effect. In some embodiments, the frequencies can fall within the ultraviolet, visible spectrum, or infrared frequency bands. In some embodiments, the optical stimulation can be applied for at least about 1, 5, 10, 30, 60, 120, 180, 240, 360, 720, 1080, 2160 seconds or more, or an amount of time falling within a range between any of the foregoing. In some embodiments, the optical stimulation can be delivered as part of a stimulation cycle including "on" periods and "off" periods.

It will be appreciated that stimulation herein can be controlled with a feedback mechanism. By way of example, in some embodiments, device wearer movement can be monitored with an IMU or other movement sensor after the application of stimulation and further stimulation can be adjusted based on detected movement.

Figure 12:
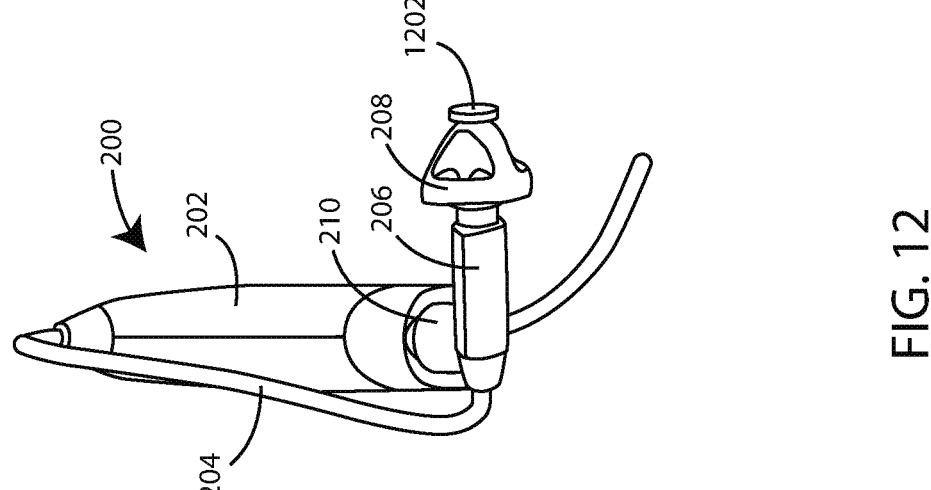
FIG. 12 is a schematic view of an ear-worn device in accordance with various embodiments herein.

Referring now to FIG. 12, a schematic view of an ear-worn device 200 in accordance with various embodiments herein. The components of the ear-worn device 200 shown in FIG. 12 are generally similar to FIG. 2. However, in FIG. 12 the ear-worn device 200 also includes a stimulation transducer 1202. The stimulation transducer 1202 can include various components depending on the nature of the stimulation to be provided.

In some embodiments, the stimulation transducer 1202 can include a heating element, which can include a metallic or ceramic material, and can produce through a Joule heating mechanism. In some embodiments, the heat can be directly conveyed from the stimulation transducer 1202 through direct contact with the device wearer. In other embodiments, the heat can be conveyed from the stimulation transducer 1202 through convection, radiation, or conduction. In some embodiments, a small fan or other device to move air can be used in order to transfer heated air from the area around the heating element to a site of stimulation of the device wearer. A site of stimulation of the device wearer can be a surface of the device wearer, such as an ear canal surface, the tympanic membrane, or the like.

In some embodiments, the stimulation transducer 1202 can include a heat sink mechanism. The heat sink mechanism can absorb heat, providing a cooling effect at a site of stimulation of the device wearer. The heat sink can be passively cooled or actively cooled, for example, by using a fan or other cooling system to further increase heat dissipation.

In some embodiments, the stimulation transducer 1202 can include an optical emitter, such as a light-emitting diode, or another light producing component. In some embodiments, the stimulation transducer 1202 can include an antenna for emission of electromagnetic fields. In some embodiments, the stimulation transducer 1202 can include one or more electrodes for electrical nerve stimulation.

In various embodiments, the ear-worn device 200 can specifically be configured to monitor device wearer movement with a movement sensor, identify a movement pattern consistent with an equilibrium disorder, estimate the characteristics of the equilibrium disorder of, and apply stimulation to at least one of the right ear, left ear, and brainstem using an ear-worn device.

Figure 13:
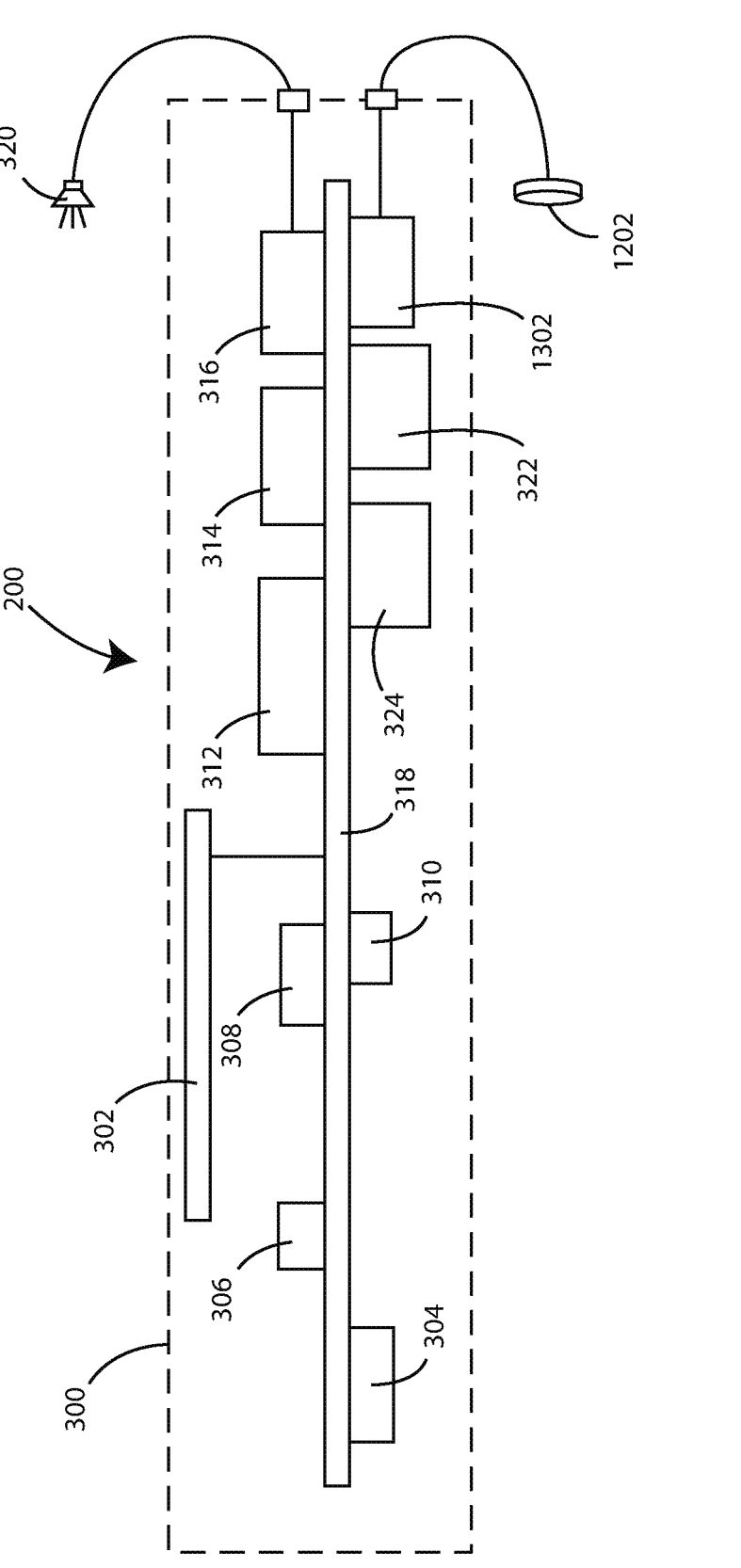
FIG. 13 is a schematic view of various components of an ear-worn device in accordance with various embodiments herein.

Referring now to FIG. 13 is a schematic view of various components of an ear-worn device 200 in accordance with various embodiments herein. The components of the ear-worn device 200 shown in FIG. 13 are generally similar to FIG. 3. However, FIG. 13 also shows a stimulation channel controller 1302. The stimulation channel controller 1302 can control stimulation delivered through the stimulation transducer 1002. The stimulation channel controller 1302 can include components such as amplifiers, capacitors, resistors, inductors and the like in order to regulate current and/or control signals sent to the stimulation transducer 1002.

Sensors

Ear-worn devices as well as medical devices herein can include one or more sensor packages (including one or more discrete or integrated sensors) to provide data. The sensor package can comprise one or a multiplicity of sensors. In some embodiments, the sensor packages can include one or more motion sensors amongst other types of sensors. Motion sensors herein can include inertial measurement units (IMU), accelerometers, gyroscopes, barometers, altimeters, and the like. In some embodiments, acoustic sensors such as MEMS microphones may be used to sense aspects of sounds and vibrations that relate to motions, such as footfalls. The IMU can be of a type disclosed in commonly owned U.S. patent application Ser. No. 15/331,230, filed Oct. 21, 2016, which is incorporated herein by reference. Motions sensors can be used to track movement of a patient in accordance with various embodiments herein.

In some embodiments, the motion sensors can be disposed in a fixed position with respect to the head of a patient, such as worn on or near the head or ears. In some embodiments, motion sensors and a microphone can be collocated within a housing forming part of an ear-worn device. In some embodiments, the motion sensors can be worn on or near another part of the body such as on a wrist, arm, or leg of the patient.

According to various embodiments, the sensor package can include one or more of an IMU, and accelerometer (3, 6, or 9 axis), a gyroscope, a barometer, an altimeter, a magnetometer, a magnetic sensor, an eye movement sensor, a pressure sensor, an acoustic sensor, a telecoil, a heart rate sensor, a global positioning system (GPS), a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (EMG), a heart rate monitor, a pulse oximeter, a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, the sensor package can be part of an ear-worn device. However, in some embodiments, the sensor packages can include one or more additional sensors that are external to an ear-worn device. For example, various of the sensors described above can be part of a wrist-worn or ankle-worn sensor package, or a sensor package supported by a chest strap.

Data produced by the sensor(s) of the sensor package can be operated on by a processor of the device or system.

As used herein the term "inertial measurement unit" or "IMU" shall refer to an electronic device that can generate signals related to a body's specific force and/or angular rate. IMUs herein can include one or more accelerometers (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

The temperature sensor can be, for example, a thermistor (thermally sensitive resistor), a resistance temperature detector, a thermocouple, a semiconductor-based sensor, an infrared sensor, or the like.

The blood pressure sensor can be, for example, a pressure sensor. The heart rate sensor can be, for example, an electrical signal sensor, an acoustic sensor, a pressure sensor, an infrared sensor, an optical sensor, or the like.

The oxygen saturation sensor (such as a blood oximetry sensor) can be, for example, an optical sensor, an infrared sensor, or the like.

The electrical signal sensor can include two or more electrodes and can include circuitry to sense and record electrical signals including sensed electrical potentials and the magnitude thereof (according to Ohm's law where V=IR) as well as measure impedance from an applied electrical potential.

It will be appreciated that the sensor package can include one or more sensors that are external to the ear-worn device. In addition to the external sensors discussed hereinabove, the sensor package can comprise a network of body sensors (such as those listed above) that sense movement of a multiplicity of body parts (e.g., arms, legs, torso). In some embodiments, the ear-worn device can be in electronic communication with the sensors or processor of another medical device, e.g., an insulin pump device or a heart pacemaker device.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method of treating an equilibrium disorder comprising:

monitoring movement of an ear-worn device wearer with a movement sensor integrated into an ear-worn device that is configured to be at least partially inserted into an ear canal of the device wearer;

identifying a movement pattern consistent with an equilibrium disorder;

estimating characteristics of the equilibrium disorder;

identifying that the movement pattern is consistent with sustained cyclical strides; and applying auditory stimulation to at least one of the right ear, left ear, or brainstem of the ear-worn device wearer at a cyclical frequency using an electroacoustic transducer of the ear-worn device, wherein the cyclical frequency equals an ambulatory pace.

2. The method of claim 1, the characteristics of the equilibrium disorder relating to at least one of a site of a lesion, the ear-worn device wearer's perceived head position versus actual head position, and the ear-worn device wearer's perceived head movement versus actual head movement.

3. The method of claim 1, further comprising measuring signals associated with a directional movement in the horizontal plane of the device wearer; and measuring a stride length of the device wearer based on the identified phases of the stride cycle and the directional movement of the device wearer.

4. The method of claim 1, wherein identifying a movement pattern consistent with sustained cyclical strides comprises identifying a movement pattern consistent with sustained cyclical strides that is sustained for at least 3 seconds.

5. The method of claim 1, further comprising analyzing data from the movement sensor to determine a sustained cyclical stride pace of the device wearer; and applying cyclical auditory stimulation to at least one of the right or left ear using the ear-worn device at a pace that is faster than the determined sustained cyclical stride pace when the determined sustained cyclical stride pace is below a threshold value.

6. The method of claim 1, further comprising adaptively determining a threshold value for the device wearer; and applying cyclical auditory stimulation to at least one of the right or left ear using the ear-worn device at a pace that is slower than the determined sustained cyclical stride pace when the determined sustained cyclical stride pace is above a threshold value.

7. The method of claim 1, wherein identifying that the movement pattern is consistent with sustained cyclical strides is performed using a microphone that is integrated into the ear-worn device.

8. The method of claim 1, further comprising:

identifying phases in the sustained cyclical strides; and detecting a shuffling-type gait by detecting variability in a timing of the phases of the sustained cyclical strides that cross a predetermined threshold value.

9. An ear-worn device system comprising:
an ear-worn device comprising
    a control circuit;
    a sensor package in communication with the control
        circuit;
    a power supply circuit in electrical communication with
        the control circuit;
    wherein a portion of the ear-worn device is configured
        to be inserted into a first ear canal of an ear-worn
        device wearer;
a second ear-worn device comprising:
    a second control circuit;
    a second sensor package in communication with the
        control circuit;
    a second power supply circuit in electrical communi-
        cation with the control circuit;
    wherein a portion of the second ear-worn device is
        configured to be inserted into a second ear canal of
        the ear-worn device wearer;
wherein the system is configured to
monitor ear-worn device wearer movement with a move-
    ment sensor integrated into the ear-worn device;
identify a movement pattern consistent with an equilib-
    rium disorder;
estimate the characteristics of the equilibrium disorder;
determine that the equilibrium disorder originates from
    one of the first ear or the second ear; and
apply stimulation differentially based on the determina-
    tion of the origin of the equilibrium disorder, the
    stimulation comprising at least one of caloric stimula-
    tion, nerve stimulation, auditory stimulation, electro-
    magnetic stimulation, and optical stimulation.

10. The system of claim 9, wherein the system is further
configured to monitor the ear-worn device wearer movement
with the movement sensor after the application of stimula-
tion and adjusting ongoing application of stimulation based
on detected movement.

11. The system of claim 10, the ear-worn device wearer
movement comprising eye movement.

12. The system of claim 10, the movement pattern com-
prising nystagmus.

13. The system of claim 9, wherein estimating the char-
acteristics of the equilibrium disorder includes estimating
the lateral distribution of the equilibrium disorder.

14. The system of claim 9, wherein estimating the char-
acteristics of an equilibrium disorder comprises determining
aspects of nystagmus including two or more of a fast phase
velocity, a slow phase velocity, a direction of nystagmus
beating, a directional preponderance, and a gaze angle.

15. The system of claim 9, the ear-worn device further
comprising a heating element or a heat sink.

16. The system of claim 9, the ear-worn device further
comprising an earbud configured to be inserted into an ear
canal of the ear-worn device wearer.

17. The system of claim 16, the earbud comprising a
stimulation transducer configured to apply the stimulation to
the ear-worn device wearer.

18. The system of claim 9, wherein the system is further
configured to, upon determining that the equilibrium disor-
der originates from the first ear, applying a higher level of
stimulation to the first ear than to the second ear.

19. The system of claim 9, wherein the system is further
configured to, upon determining that the equilibrium disor-
der originates from the first ear, applying a different type of
stimulation to the first ear than to the second ear.

20. The system of claim 9, wherein the system is further
configured to:
    determine that the equilibrium disorder originates the first
        ear; and
    apply stimulation differentially to the first ear.

* * * * *